United States Patent
Mooney et al.

(10) Patent No.: US 10,695,468 B2
(45) Date of Patent: *Jun. 30, 2020

(54) SCAFFOLDS FOR CELL COLLECTION OR ELIMINATION

(71) Applicant: President and Fellows of Harvard College, Cambridge, MA (US)

(72) Inventors: David J. Mooney, Sudbury, MA (US); Omar Abdel-Rahman Ali, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/696,938

(22) Filed: Sep. 6, 2017

(65) Prior Publication Data
US 2018/0036454 A1   Feb. 8, 2018

Related U.S. Application Data

(63) Continuation of application No. 12/665,761, filed as application No. PCT/US2008/007258 on Jun. 11, 2008, now Pat. No. 9,770,535.

(60) Provisional application No. 60/936,743, filed on Jun. 21, 2007.

(51) Int. Cl.
| | | |
|---|---|---|
| *A61L 27/56* | (2006.01) | |
| *A61L 27/50* | (2006.01) | |
| *A61L 27/54* | (2006.01) | |

(52) U.S. Cl.
CPC ........... *A61L 27/56* (2013.01); *A61L 27/50* (2013.01); *A61L 27/54* (2013.01); *A61L 2300/252* (2013.01); *A61L 2300/404* (2013.01); *A61L 2300/44* (2013.01); *A61L 2300/45* (2013.01); *A61L 2300/64* (2013.01)

(58) Field of Classification Search
CPC .......... A61L 27/56; A61L 27/50; A61L 27/54; A61L 2300/45; A61L 2300/404; A61L 2300/64; A61L 2300/44; A61L 2300/252
See application file for complete search history.

(56) References Cited

U.S. PATENT DOCUMENTS

| | | | |
|---|---|---|---|
| 3,773,919 A | 11/1973 | Boswell et al. | |
| 4,522,811 A | 6/1985 | Eppstein et al. | |
| 4,946,778 A | 8/1990 | Ladner et al. | |
| 5,073,627 A | 12/1991 | Curtis et al. | |
| 5,091,513 A | 2/1992 | Huston et al. | |
| 5,132,405 A | 7/1992 | Huston et al. | |
| 5,885,829 A | 3/1999 | Mooney et al. | |
| 5,888,987 A | 3/1999 | Haynes et al. | |
| 6,129,716 A | 10/2000 | Steer | |
| 6,193,970 B1 | 2/2001 | Pardoll et al. | |
| 6,251,396 B1 | 6/2001 | Gaur et al. | |
| 6,281,256 B1 | 8/2001 | Harris et al. | |
| 6,334,968 B1 | 1/2002 | Shapiro et al. | |
| 6,403,374 B1 | 6/2002 | Tsien et al. | |
| 6,429,199 B1 | 8/2002 | Krieg et al. | |
| 6,511,650 B1 | 1/2003 | Eiselt et al. | |
| 6,541,022 B1 | 4/2003 | Murphy et al. | |
| 6,642,363 B1 | 11/2003 | Mooney et al. | |
| 6,685,963 B1 | 2/2004 | Taupin et al. | |
| 6,748,954 B2 | 6/2004 | Lee et al. | |
| 6,767,928 B1 | 7/2004 | Murphy et al. | |
| 6,783,712 B2 | 8/2004 | Slivka et al. | |
| 6,790,840 B1 | 9/2004 | Lee et al. | |
| 6,797,738 B2 | 9/2004 | Harris et al. | |
| 6,800,733 B2 | 10/2004 | Tsien et al. | |
| 7,157,566 B2 | 1/2007 | Tsien et al. | |
| 7,186,413 B2 | 3/2007 | Bouhadir et al. | |
| 7,192,693 B2 | 3/2007 | Bryant et al. | |
| 7,427,602 B1 | 9/2008 | Shea et al. | |
| 7,575,759 B2 | 8/2009 | Murphy et al. | |
| 7,687,241 B2 | 3/2010 | Chen | |
| 7,790,699 B2 | 9/2010 | Melvik et al. | |
| 8,067,237 B2 * | 11/2011 | Mooney | A61L 27/3633 435/307.1 |
| 8,188,058 B2 | 5/2012 | Hackam et al. | |
| 8,273,373 B2 | 9/2012 | Alsberg et al. | |
| 8,709,464 B2 | 4/2014 | Ma et al. | |
| 8,728,456 B2 | 5/2014 | Sands et al. | |
| 8,932,583 B2 | 1/2015 | Mooney et al. | |

(Continued)

FOREIGN PATENT DOCUMENTS

| | | |
|---|---|---|
| CN | 101655611 A | 2/2010 |
| EP | 0562862 A1 | 9/1993 |

(Continued)

OTHER PUBLICATIONS

Abrahams et al., Expression and secretion of antiviral factors by trophoblast cells following stimulation by the TLR-3 agonist, Poly(I : C). Hum Reprod. Sep. 2006;21(9):2432-9.

Agache et al., Mechanical properties and Young's modulus of human skin in vivo. Arch Dermatol Res. 1980;269(3):221-32.

Agrawal et al., Cutting edge: different Toll-like receptor agonists instruct dendritic cells to induce distinct Th responses via differential modulation of extracellular signal-regulated kinase-mitogen-activated protein kinase and c-Fos. J Immunol. Nov. 15. 2003;171(10):4984-9.

(Continued)

*Primary Examiner* — Robert S Cabral
(74) *Attorney, Agent, or Firm* — McCarter & English, LLP; Maria Laccotripe Zacharakis; Weiguo Zhou

(57) ABSTRACT

A device that includes a scaffold composition and a bioactive composition with the bioactive composition being incorporated therein or thereon, or diffusing from the scaffold composition such that the scaffold composition and/or a bioactive composition captures and eliminates undesirable cells from the body a mammalian subject. The devices mediate active recruitment, sequestration, and removal or elimination of undesirable cells from their host.

26 Claims, No Drawings
Specification includes a Sequence Listing.

(56) References Cited

U.S. PATENT DOCUMENTS

| | | |
|---|---|---|
| 9,012,399 B2 | 4/2015 | Cao et al. |
| 9,132,210 B2 | 9/2015 | Mooney et al. |
| 9,770,535 B2 | 9/2017 | Mooney et al. |
| 2002/0131853 A1 | 9/2002 | Nagasawa |
| 2002/0150604 A1 | 10/2002 | Yi et al. |
| 2003/0075822 A1 | 4/2003 | Slivka et al. |
| 2003/0082806 A1 | 5/2003 | Berenson et al. |
| 2003/0095994 A1 | 5/2003 | Geistlich et al. |
| 2003/0100527 A1 | 5/2003 | Krieg et al. |
| 2003/0232895 A1 | 12/2003 | Omidian et al. |
| 2004/0058883 A1 | 3/2004 | Phillips et al. |
| 2004/0063206 A1 | 4/2004 | Rowley et al. |
| 2004/0136968 A1 | 7/2004 | Zheng et al. |
| 2004/0151764 A1 | 8/2004 | Zamora |
| 2004/0220111 A1 | 11/2004 | Kleinman et al. |
| 2004/0242469 A1 | 12/2004 | Lee et al. |
| 2004/0242482 A1 | 12/2004 | Gehring et al. |
| 2005/0002915 A1 | 1/2005 | Atala et al. |
| 2005/0037330 A1 | 2/2005 | Fischer et al. |
| 2005/0053667 A1 | 3/2005 | Irvine et al. |
| 2005/0079159 A1 | 4/2005 | Shastri et al. |
| 2005/0090008 A1 | 4/2005 | Segura et al. |
| 2005/0106211 A1 | 5/2005 | Nelson et al. |
| 2005/0154376 A1 | 7/2005 | Riviere et al. |
| 2005/0177249 A1 | 8/2005 | Kladakis et al. |
| 2005/0202394 A1 | 9/2005 | Dobson |
| 2006/0083712 A1 | 4/2006 | Anversa |
| 2006/0141018 A1 | 6/2006 | Cochrum et al. |
| 2006/0264380 A1 | 11/2006 | Hellstrom et al. |
| 2006/0292134 A1 | 12/2006 | Stohs |
| 2007/0003595 A1 | 1/2007 | Wang et al. |
| 2007/0020232 A1 | 1/2007 | Rossignol et al. |
| 2007/0026518 A1 | 2/2007 | Healy et al. |
| 2007/0081972 A1 | 4/2007 | Sandler et al. |
| 2007/0116680 A1 | 5/2007 | Stegemann et al. |
| 2007/0178159 A1 | 8/2007 | Chen et al. |
| 2007/0190646 A1 | 8/2007 | Engler et al. |
| 2008/0020011 A1* | 1/2008 | Finkelstein ............ A61L 27/34 424/423 |
| 2008/0044900 A1 | 2/2008 | Mooney et al. |
| 2008/0044990 A1 | 2/2008 | Lee |
| 2008/0051490 A1 | 2/2008 | Williams et al. |
| 2008/0138416 A1 | 6/2008 | Rauh et al. |
| 2008/0152624 A1 | 6/2008 | Paludan et al. |
| 2008/0206308 A1 | 8/2008 | Jabbari et al. |
| 2008/0268052 A1 | 10/2008 | Voytik-Harbin et al. |
| 2009/0017096 A1 | 1/2009 | Lowman et al. |
| 2009/0192079 A1 | 7/2009 | Santos et al. |
| 2009/0238853 A1 | 9/2009 | Liu et al. |
| 2009/0297579 A1 | 12/2009 | Semino et al. |
| 2009/0305983 A1 | 12/2009 | Ying et al. |
| 2010/0015709 A1 | 1/2010 | Rehfeldt et al. |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0159008 A1 | 6/2010 | Barron et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0117170 A1 | 5/2011 | Cao et al. |
| 2012/0100182 A1 | 4/2012 | Mooney et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264599 A1 | 10/2012 | Komatsu et al. |
| 2012/0329791 A1 | 12/2012 | Ashwell et al. |
| 2013/0029030 A1 | 1/2013 | Larsen |
| 2013/0177536 A1 | 7/2013 | Mooney et al. |
| 2013/0202707 A1 | 8/2013 | Ali et al. |
| 2013/0302396 A1 | 11/2013 | Mooney et al. |
| 2013/0331343 A1 | 12/2013 | Cao et al. |
| 2014/0079752 A1 | 3/2014 | Huebsch et al. |
| 2014/0112990 A1 | 4/2014 | Bencherif et al. |
| 2014/0178964 A1 | 6/2014 | Mooney et al. |
| 2014/0193488 A1 | 7/2014 | Kim et al. |
| 2014/0227327 A1 | 8/2014 | Bencherif et al. |
| 2014/0234423 A1 | 8/2014 | Sands et al. |
| 2015/0024026 A1 | 1/2015 | Mooney et al. |
| 2015/0072009 A1 | 3/2015 | Kim et al. |

FOREIGN PATENT DOCUMENTS

| | | | |
|---|---|---|---|
| EP | 1452191 | A2 | 9/2004 |
| EP | 1561481 | A2 | 8/2005 |
| JP | 2004-520043 | A | 7/2004 |
| JP | 2005-170816 | A | 6/2005 |
| JP | 2007-500673 | A | 1/2007 |
| JP | 2007-503881 | A | 3/2007 |
| JP | 2007-528848 | A | 10/2007 |
| JP | 2009-519042 | A | 5/2009 |
| JP | 2009-521406 | A | 6/2009 |
| JP | 2009-540921 | A | 11/2009 |
| JP | 2010-508976 | A | 3/2010 |
| WO | WO-1996/16086 | A1 | 5/1996 |
| WO | WO-1998/012228 | A1 | 3/1998 |
| WO | WO-1999/51259 | A2 | 10/1999 |
| WO | WO-2001/35932 | A2 | 5/2001 |
| WO | WO-2002/16557 | A2 | 2/2002 |
| WO | WO-2002/058723 | A2 | 8/2002 |
| WO | WO-2003/020884 | A2 | 3/2003 |
| WO | WO-2004/006990 | A2 | 1/2004 |
| WO | WO-2004/030706 | A2 | 4/2004 |
| WO | WO-2004/089413 | A1 | 10/2004 |
| WO | WO-2005/013896 | A2 | 2/2005 |
| WO | WO-2005/013933 | A1 | 2/2005 |
| WO | WO-2005/026318 | A2 | 3/2005 |
| WO | WO-2005/037190 | A2 | 4/2005 |
| WO | WO-2005/037293 | A1 | 4/2005 |
| WO | WO-2005/046748 | A1 | 5/2005 |
| WO | WO-2005/072088 | A2 | 8/2005 |
| WO | WO-2006/119619 | A1 | 11/2006 |
| WO | WO-2006/136905 | A2 | 12/2006 |
| WO | WO-2007/030901 | A1 | 3/2007 |
| WO | WO-2007/063075 | A1 | 6/2007 |
| WO | WO-2007/064152 | A1 | 6/2007 |
| WO | WO-2007/070660 | A2 | 6/2007 |
| WO | WO-2007/078196 | A1 | 7/2007 |
| WO | WO-2007/107739 | A1 | 9/2007 |
| WO | WO-2007/150020 | A1 | 12/2007 |
| WO | WO-2008/018707 | A1 | 2/2008 |
| WO | WO-2008/109852 | A2 | 9/2008 |
| WO | WO-2008/114149 | A2 | 9/2008 |
| WO | WO-2008/148761 | A1 | 12/2008 |
| WO | WO-2008/157394 | A2 | 12/2008 |
| WO | WO-2009/005769 | A2 | 1/2009 |
| WO | WO-2009/018500 | A1 | 2/2009 |
| WO | WO-2009/072767 | A2 | 6/2009 |
| WO | WO-2009/074341 | A1 | 6/2009 |
| WO | WO-2009/102465 | A2 | 8/2009 |
| WO | WO-2009/146456 | A1 | 12/2009 |
| WO | WO-2009/155583 | A1 | 12/2009 |
| WO | WO-2010/078209 | A2 | 7/2010 |
| WO | WO-2010/120749 | A2 | 10/2010 |
| WO | WO-2011/014871 | A1 | 2/2011 |
| WO | WO-2011/063336 | A2 | 5/2011 |
| WO | WO-2011/109834 | A2 | 9/2011 |
| WO | WO-2011/130753 | A2 | 10/2011 |
| WO | WO-2011/150240 | A1 | 12/2011 |
| WO | WO-2011/151431 | A1 | 12/2011 |
| WO | WO-2011/163669 | A2 | 12/2011 |
| WO | WO-2012/009611 | A2 | 1/2012 |
| WO | WO-2012/019049 | A1 | 2/2012 |
| WO | WO-2012/048165 | A2 | 4/2012 |
| WO | WO-2012/064697 | A2 | 5/2012 |
| WO | WO-2012/148684 | A1 | 11/2012 |
| WO | WO-2012/149358 | A1 | 11/2012 |
| WO | WO-2012/167230 | A1 | 12/2012 |

(56) References Cited

FOREIGN PATENT DOCUMENTS

| WO | WO-2013/106852 A1 | 7/2013 |
|---|---|---|
| WO | WO-2013/158673 A1 | 10/2013 |

OTHER PUBLICATIONS

Aguado et al., Improving viability of stem cells during syringe needle flow through the design of hydrogel cell carriers. Tissue Eng Part A. Apr. 2012;18(7-8):806-15.
Akira et al., Pathogen recognition and innate immunity. Cell. Feb. 24, 2006;124(4):783-801.
Akira et al., Toll-like receptors: critical proteins linking innate and acquired immunity. Nat Immunol. Aug. 2001;2(8):675-80.
Akpalo et al., Fibrin-polyethylene oxide interpenetrating polymer networks: new self-supported biomaterials combining the properties of both protein gel and synthetic polymer. Acta Biomater. Jun. 2011;7(6):2418-27.
Aldhous, Print Me a Heart and a Set of Arteries. New Scientist. 2006;2547:19.
Ali et al., Controlled Local Delivery of GM-CSF From Polymer-Based Vaccines Enhances Anti-Tumor Immune Responses by Priming Host Dendritic Cells. 2007 AACR Annual Meeting. 2007;48:652, Abstract #2736.
Ali et al., Converging Cell Therapy with Biomaterials. Cell Transplantation from Laboratory to Clinic. 2006:591-609.
Ali et al. In situ regulation of DC subsets and T cells mediates tumor regression in mice. Sci Transl Med. Nov. 25, 2009;1(8):8-19.
Ali et al. Infection-mimicking materials to program dendritic cells in situ. Nat Mater. Feb. 2009;8(2): 51-8.
Ali et al., Sustained GM-CSF and PEI condensed pDNA presentation increases the level and duration of gene expression in dendritic cells. J Control Release. Dec. 18, 2008;132(3):273-8.
Allen et al., Regulation of satellite cells during skeletal muscle growth and development. Proc Soc Exp Biol Med. Jun. 1990;194(2):81-6.
Allen et al., Regulation of skeletal muscle satellite cell proliferation by bovine pituitary fibroblast growth factor. Exp Cell Res. May 1984;152(1):154-60.
Almarza et al., Evaluation of three growth factors in combinations of two for temporomandibular joint disc tissue engineering. Arch Oral Biol. Mar. 2006;51(3):215-21.
Alsberg et al., Cell-interactive alginate hydrogels for bone tissue engineering. J Dent Res. Nov. 2001;80(11):2025-9.
Alsberg et al., Engineering growing tissues. Proc Natl Acad Sci U S A. Sep. 17, 2002;99(19):12025-30.
Alsberg et al., Regulating bone formation via controlled scaffold degradation. J Dent Res. Nov. 2003;82(11):903-8.
American Diabetes Association, Standards of Medical Care in Diabetes—2013. Diabetes Care. 2013;36(S1):S11-S66.
Anderson et al., Biomaterial microarrays: rapid, microscale screening of polymer-cell interaction. Biomaterials. Aug. 2005;26(23):4892-7.
Anderson et al., Nanoliter-scale synthesis of arrayed biomaterials and application to human embryonic stem cells. Nat Biotechnol. Jul. 2004;22(7):863-6.
Anderson et al., The NOD mouse: a model of immune dysregulation. Annu Rev Immunol. 2005;23:447-85.
Anderson, A role for nitric oxide in muscle repair: nitric oxide-mediated activation of muscle satellite cells. Mol Biol Cell. May 2000;11(5):1859-74.
Annual Review. 2008:122-131.
Arany et al., At the edge of translation—materials to program cells for directed differentiation. Oral Dis. Apr. 2011;17(3):241-51.
Aschner et al., Metabolic memory for vascular disease in diabetes. Diabetes Technol Ther. Jun. 2012;14 Suppl 1:S68-74.
Atala et al., Endoscopic treatment of vesicoureteral reflux with a chondrocyte-alginate suspension. J Urol. Aug. 1994;152(2 Pt 2):641-3.
Aubin et al., Directed 3D cell alignment and elongation in microengineered hydrogels. Biomaterials. Sep. 2010;31(27):6941-6951.
Augst et al., Alginate hydrogels as biomaterials. Macromol Biosci. Aug. 7, 2006;6(8):623-33.
Bachelder et al., Acid-degradable polyurethane particles for protein-based vaccines: biological evaluation and in vitro analysis of particle degradation products. Mol Pharm. Sep.-Oct. 2008;5(5):876-84.
Bachem et al., Superior antigen cross-presentation and XCR1 expression define human CD11c+CD141+ cells as homologues of mouse CD8+ dendritic cells. J Exp Med. Jun. 7, 2010;207(6):1273-81.
Badovinac et al., Regulation of CD8+ T cells undergoing primary and secondary responses to infection in the same host. J Immunol. May 15, 2003;170(10):4933-42.
Bakri et al., Pharmacokinetics of intravitreal bevacizumab (Avastin). Ophthalmology. May 2007;114(5):855-9.
Balakrishna et al., Structural correlates of antibacterial and membrane-permeabilizing activities in acylpolyamines. Antimicrob Agents Chemother. Mar. 2006;50(3):852-61.
Banchereau et al., Dendritic cells and the control of immunity. Nature. Mar. 19, 1998;392(6673):245-52.
Bar-Cohen et al., Electroactive Polymer Actuators and Sensors. MRS Bullet. 2008;33(3):173-181.
Bar-Or et al., Induction of antigen-specific tolerance in multiple sclerosis after immunization with DNA encoding myelin basic protein in a randomized, placebo-controlled phase 1/2 trial. Arch Neurol. Oct. 2007;64(10):1407-15.
Barbero et al., Growth factor supplemented matrigel improves ectopic skeletal muscle formation—a cell therapy approach. J Cell Physiol. Feb. 2001;186(2):183-92.
Barrio et al., A two-dimensional numerical study of spatial pattern formation in interacting Turing systems. Bull Math Biol. May 1999;61(3):483-505.
Bates, Improved muscle regeneration by combining VEGF with IGF1 . Regen Med. Nov. 2010;5(6):853-4.
Beaucage et al., The Functionalization of Oligonucleotides via Phosphoramidite Derivatives. Tetrahedron. Mar. 5, 1993;49(10):1925-1963.
Beauchamp et al., Dynamics of myoblast transplantation reveal a discrete minority of precursors with stem cell-like properties as the myogenic source. J Cell Biol. Mar. 22, 1999;144(6):1113-22.
Becker et al., Cytological demonstration of the clonal nature of spleen colonies derived from transplanted mouse marrow cells. Nature. Feb. 2, 1963;197:452-4.
Beebe et al., Functional hydrogel structures for autonomous flow control inside microfluidic channels. Nature. Apr. 6, 2000;404(6778):588-90.
Bekiari et al., Study of poly(N,N-dimethylacrylamide)/CdS nanocomposite organic/inorganic gels. Langmuir. Sep. 14, 2004;20(19):7972-5.
Bell, Models for the specific adhesion of cells to cells. Science. May 12, 1978;200(4342):618-27.
Bencherif et al., End-group effects on the properties of PEG-co-PGA hydrogels. Acta Biomater. Jul. 2009;5(6):1872-83.
Bencherif et al., Influence of cross-linker chemistry on release kinetics of PEG-co-PGA hydrogels. J Biomed Mater Res A. Jul. 2009;90(1):142-53.
Bencherif et al., Influence of the degree of methacrylation on hyaluronic acid hydrogels properties. Biomaterials. Apr. 2008;29(12):1739-49.
Bencherif et al., Injectable preformed scaffolds with shape-memory properties. Proc Natl Acad Sci U S A. Nov. 27, 2012;109(48):19590-5.
Bencherif et al., Nanostructured hybrid hydrogels prepared by a combination of atom transfer radical polymerization and free radical polymerization. Biomaterials. Oct. 2009;30(29):5270-8.
Bencherif et al., Synthesis by AGET ATRP of degradable nanogel precursors for in situ formation of nanostructured hyaluronic acid hydrogel. Biomacromolecules. Sep. 14, 2009;10(9):2499-507.

(56) References Cited

OTHER PUBLICATIONS

Benton et al., Photocrosslinking of gelatin macromers to synthesize porous hydrogels that promote valvular interstitial cell function. Tissue Eng Part A. Nov. 2009;15(11):3221-30.
Berg et al., Il-10 is a central regulator of cyclooxygenase-2 expression and prostaglandin production. J Immunol. Feb. 15, 2001;166(4):2674-80.
Bergstraesser et al., Stimulation and inhibition of human mammary epithelial cell duct morphogenesis in vitro. Proc Assoc Am Physicians. Mar. 1996;108(2):140-54.
Bianco et al., The meaning, the sense and the significance: translating the science of mesenchymal stem cells into medicine. Nat Med. Jan. 2013;19(1):35-42.
Bilodeau et al., Regular Pyramid Punch Problem. J Appl Mech. 1992;59(3):519-523.
Bischoff, Proliferation of muscle satellite cells on intact myofibers in culture. Dev Biol. May 1986;115(1):129-39.
Blanas et al., Induction of autoimmune diabetes by oral administration of autoantigen. Science. Dec. 6, 1996;274(5293):1707-9.
Blumenthal et al., Polyurethane scaffolds seeded with genetically engineered skeletal myoblasts: a promising tool to regenerate myocardial function. Artif Organs. Feb. 2010;34(2):E46-54.
Boateng et al., Wound healing dressings and drug delivery systems: a review. J Pharm Sci. Aug. 2008;97(8):2892-923.
Boerckel et al., Mechanical regulation of vascular growth and tissue regeneration in vivo. Proc Natl Acad Sci USA. Sep. 13, 2011;108(37):E674-80.
Bohl et al., Role of synthetic extracellular matrix in development of engineered dental pulp. J Biomater Sci Polym Ed. 1998;9(7):749-64.
Bonauer et al., MicroRNA-92a controls angiogenesis and functional recovery of ischemic tissues in mice. Science. Jun. 26, 2009;324(5935):1710-3.
Boontheekul et al., Controlling alginate gel degradation utilizing partial oxidation and bimodal molecular weight distribution. Biomaterials. May 2005;26(15):2455-65.
Boontheekul et al., Regulating myoblast phenotype through controlled gel stiffness and degradation. Tissue Eng. Jul. 2007;13(7):1431-42.
Borselli et al., Functional muscle regeneration with combined delivery of angiogenesis and myogenesis factors. Proc Natl Acad Sci U S A. Feb. 23, 2010;107(8):3287-92.
Bouhadir et al., Degradation of partially oxidized alginate and its potential application for tissue engineering. Biotechnol Prog. Sep.-Oct. 2001;17(5):945-50.
Bouhadir et al., Synthesis of Cross-Linked Poly(aldehyde guluronate) Hydrogels. Polymer. Jun. 1999;40(12):3575-3584.
Bowne et al., Injection of DNA encoding granulocyte-macrophage colony-stimulating factor recruits dendritic cells for immune adjuvant effects. Cytokines Cell Mol Ther. Dec. 1999;5(4):217-25.
Brignone et al., A phase I pharmacokinetic and biological correlative study of IMP321, a novel MHC class II agonist, in patients with advanced renal cell carcinoma. Clin Cancer Res. Oct. 1, 2009;15(19):6225-31.
Brinkman et al., Photo-cross-linking of type I collagen gels in the presence of smooth muscle cells: mechanical properties, cell viability, and function. Biomacromolecules. Jul.-Aug. 2003;4(4):890-5.
Brinkmann et al., Neutrophil extracellular traps kill bacteria. Science. Mar. 5, 2004;303(5663):1532-5.
Brouwers et al., Can the growth factors PTHrP, Ihh and VEGF, together regulate the development of a long bone? J Biomech. 2006;39(15):2774-82.
Broxmeyer, Insights into the biology of cord blood stem/progenitor cells. Cell Prolif. Apr. 2011;44 Suppl 1:55-9.
Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;5(11):6278-86.
Bryant et al., Photo-patterning of porous hydrogels for tissue engineering. Biomaterials. Jul. 2007;28(19):2978-86.
Buckwalter et al., Form of Antigen Dictates Immunity: Irradiated Cell vs. Whole Cell Lysate Vaccination. J Immunol. Apr. 1, 2007;178(1 Suppl):S77.
Bullard et al., Fetal wound healing: current biology. World J Surg. Jan. 2003;27(1):54-61.
Buonaguro et al., Translating tumor antigens into cancer vaccines. Clin Vaccine Immunol. Jan. 2011;18(1):23-34.
Burdick et al., Controlled degradation and mechanical behavior of photopolymerized hyaluronic acid networks. Biomacromolecules. Jan.-Feb. 2005;6(1):386-91.
Burdick et al., Photoencapsulation of osteoblasts in injectable RGD-modified PEG hydrogels for bone tissue engineering. Biomaterials. Nov. 2002;23(22):4315-23.
Burdick et al., Stimulation of neurite outgrowth by neurotrophins delivered from degradable hydrogels. Biomaterials. Jan. 2006;27(3):452-9.
Burger et al., Effect of VEGF and its receptor antagonist SU-5416, an inhibitor of angiogenesis, on processing of the beta-amyloid precursor protein in primary neuronal cells derived from brain tissue of Tg2576 mice. Int J Dev Neurosci. Nov. 2010;28(7):597-604.
Bégué et al., Vaccination against human papillomavirus. Implementation and efficacy against cervical cancer control. Bull Acad Natl Med. Dec. 2007;191(9):1805-16.
Calvert, Electroactive Polymer Gels. Electroactive Polymer (EAP) Acutators as Artificial Muscle: Reality, Potential, and Challenges. Bar-Cohen, (Ed.), Spie Press, Bellingham, WA. 151-170. (2004).
Calvert, Gel Sensors and Actuators. MRS Bullet. 2008;33(3):207-212.
Cameron et al., The influence of substrate creep on mesenchymal stem cell behaviour and phenotype. Biomaterials. Sep. 2011;32(26):5979-93.
Cao et al., Promoting angiogenesis via manipulation of VEGF responsiveness with notch signaling. Biomaterials. Sep. 2009; 30(25):4085-93.
Carlson et al., Notch signaling pathway and tissue engineering. Front Biosci. Sep. 1, 2007;12:5143-56.
Carmeliet et al., Angiogenesis in cancer and other diseases. Nature. Sep. 14, 2000;407(6801):249-57.
Carmeliet, Mechanisms of angiogenesis and arteriogenesis. Nat Med. Apr. 2000;6(4):389-95.
Caulfield et al., Regulation of major histocompatibility complex class II antigens on human alveolar macrophages by granulocyte-macrophage colony-stimulating factor in the presence of glucocorticoids. Immunology. Sep. 1999;98(1):104-10.
Ceriello et al., Clinical review 2: The "metabolic memory": is more than just tight glucose control necessary to prevent diabetic complications? J Clin Endocrinol Metab. Feb. 2009;94(2):410-5.
Ceriello et al., The emerging challenge in diabetes: the "metabolic memory". Vascul Pharmacol. Nov.-Dec. 2012;57(5-6):133-8.
Chan et al., Antifibrotic effects of suramin in injured skeletal muscle after laceration. J Appl Physiol. Sep. 2003;95(2):771-80.
Chan et al., Helix induction in antimicrobial peptides by alginate in biofilms. J Biol Chem. Sep. 10, 2004;279(37):38749-54.
Chan et al., Traction dynamics of filopodia on compliant substrates. Science. Dec. 12, 2008;322(5908):1687-91.
Chang, Mouse models for studies of retinal degeneration and diseases. Methods Mol Biol. 2013;935:27-39.
Chen et al., Adipogenic differentiation of adipose tissue-derived human mesenchymal stem cells: effect of gastric bypass surgery. Surg Endosc. Dec. 2012;26(12):3449-56.
Chen et al., Functional Human Vascular Network Generated in Photocrosslinkable Gelatin Methacrylate Hydrogels. Adv Funct Mater. May 23, 2012;22(10):2027-2039.
Chen et al., Integrated approach to designing growth factor delivery systems. FASEB J. Dec. 2007;21(14):3896-903.
Chen et al., Polymeric growth factor delivery strategies for tissue engineering. Pharm Res. Aug. 2003;20(8):1103-12.
Chen et al., Skeletal muscle stem cells. Reprod Biol Endocrinol. Nov. 13, 2003;1:101.
Chen et al., Spatio-temporal VEGF and PDGF delivery patterns blood vessel formation and maturation. Pharm Res. Feb. 2007;24(2):258-64.

(56) References Cited

OTHER PUBLICATIONS

Chiang et al., Whole tumor antigen vaccines. Semin Immunol. Jun. 2010;22(3):132-43.
Choi et al., In vitro mineralization by preosteoblasts in poly(DL-lactide-co-glycolide) inverse opal scaffolds reinforced with hydroxyapatite nanoparticles. Langmuir. Jul. 20, 2010;26(14):12126-31.
Choi et al., Three-dimensional scaffolds for tissue engineering: the importance of uniformity in pore size and structure. Langmuir. Dec. 21, 2010;26(24):19001-6.
Choi, Replacement Organs, Hot Off the Press. New Scientist. 2003;177(2379):16.
Chou et al., Characterization of Photocross Linked Alginate Hydrogels for Nucleus Pulposus Cell Encapsulation. J Biomed Mater Res A. 2009;91A(1):187-194.
Chromiak et al., Bioreactor perfusion system for the long-term maintenance of tissue-engineered skeletal muscle organoids. In Vitro Cell Dev Biol Anim. Oct. 1998;34(9):694-703.
Clark et al., Myosin II and mechanotransduction: a balancing act. Trends Cell Biol. Apr. 2007;17(4):178-86.
Clauss et al., Interstitial transport of rabbit and sheep antibodies in normal and neoplastic tissues. Cancer Res. Jun. 15, 1990;50(12):3487-92.
Cohen et al., Controlled delivery systems for proteins based on poly(lactic/glycolic acid) microspheres. Pharm Res. Jun. 1991;8(6):713-20.
Comisar et al., Engineering RGD nanopatterned hydrogels to control preosteoblast behavior: a combined computational and experimental approach. Biomaterials. Oct. 2007;28(30):4409-17.
Conboy et al., The regulation of Notch signaling controls satellite cell activation and cell fate determination in postnatal myogenesis. Dev Cell. Sep. 2002;3(3):397-409.
Conconi et al., In vitro and in vivo evaluation of acellular diaphragmatic matrices seeded with muscle precursors cells and coated with VEGF silica gels to repair muscle defect of the diaphragm. J Biomed Mater Res A. May 2009;89(2):304-16.
Conn et al., Purification of a glycoprotein vascular endothelial cell mitogen from a rat glioma-derived cell line. Proc Natl Acad Sci U S A. Feb. 1990;87(4):1323-7.
Cook et al., A sialomucopeptide liberated by trypsin from the human erythrocyte. Nature. Dec. 17, 1960;188:1011-2.
Cooper et al., Extended amplification in vitro and replicative senescence: key factors implicated in the success of human myoblast transplantation. Hum Gene Ther. Aug. 10, 2003;14(12):1169-79.
Cooper, Metabolic memory: implications for diabetic vascular complications. Pediatr Diabetes. Aug. 2009;10(5):343-6.
Corcione et al., CCL19 and CXCL12 trigger in vitro chemotaxis of human mantle cell lymphoma B cells. Clin Cancer Res. Feb. 1, 2004;10(3):964-71.
Cornelison et al., Single-cell analysis of regulatory gene expression in quiescent and activated mouse skeletal muscle satellite cells. Dev Biol. Nov. 15, 1997;191(2):270-83.
Cornelison et al., Syndecan-3 and syndecan-4 specifically mark skeletal muscle satellite cells and are implicated in satellite cell maintenance and muscle regeneration. Dev Biol. Nov. 1, 2001;239(1):79-94.
Coulson et al., Flow of Fluids through Granular Beds and Packed Columns. Chemical Engineering. New York: Pergamon Press. 2(1978):125-171.
Crameri et al., Improved green fluorescent protein by molecular evolution using DNA shuffling. Nat Biotechnol. Mar. 1996;14(3):315-9.
Cuda et al., In vitro actin filament sliding velocities produced by mixtures of different types of myosin. Biophys J. Apr. 1997;72(4):1767-79.
Cukierman et al., Taking cell-matrix adhesions to the third dimension. Science. Nov. 23, 2001;294(5547):1708-12.
Cullen et al., Investigation of vascular endothelial growth factor effects on pulmonary endothelial monolayer permeability and neutrophil transmigration. Gen Pharmacol. Sep. 2000;35(3):149-57.

Curiel et al., Tumor immunotherapy: inching toward the finish line. J Clin Invest. Feb. 2002;109(3):311-2.
D'Amico et al., The early progenitors of mouse dendritic cells and plasmacytoid predendritic cells are within the bone marrow hemopoietic precursors expressing Flt3. J Exp Med. Jul. 21, 2003;198(2):293-303.
Dar et al., Optimization of cardiac cell seeding and distribution in 3D porous alginate scaffolds. Biotechnol Bioeng. Nov. 5, 2002;80(3):305-12.
Daro et al., Polyethylene glycol-modified GM-CSF expands CD11b(high)CD11c(high) but not CD11b(low)CD11c(high) murine dendritic cells in vivo: a comparative analysis with Flt3 ligand. J Immunol. Jul. 1, 2000;165(1):49-58.
David et al., The in vitro Desensitization of Sensitive Cells by Trypsin. J Exp Med. Dec. 1, 1964;120:1189-200.
Davies et al., Antibody-antigen complexes. Annu Rev Biochem. 1990;59:439-73.
De Jong et al., Regulation of Notch signaling genes during BMP2-induced differentiation of osteoblast precursor cells. Biochem Biophys Res Commun. Jul. 16, 2004;320(1):100-7.
De Temmerman et al., Particulate vaccines: on the quest for optimal delivery and immune response. Drug Discov Today. Jul. 2011;16(13-14):569-82.
Dembo et al., Stresses at the cell-to-substrate interface during locomotion of fibroblasts. Biophys J. Apr. 1999;76(4):2307-16.
Den Haan et al., CD8(+) but not CD8(−) dendritic cells cross-prime cytotoxic T cells in vivo. J Exp Med. Dec. 18, 2000 18;192(12):1685-96.
Dennis et al., Excitability and contractility of skeletal muscle engineered from primary cultures and cell lines. Am J Physiol Cell Physiol. Feb. 2001;280(2):C288-95.
Dennis et al., Excitability and isometric contractile properties of mammalian skeletal muscle constructs engineered in vitro. In Vitro Cell Dev Biol Anim. May 2000;36(5):327-35.
Dexter et al., Conditions controlling the proliferation of haemopoietic stem cells in vitro. J Cell Physiol. Jun. 1977;91(3):335-44.
Di Nicola et al., Human bone marrow stromal cells suppress T-lymphocyte proliferation induced by cellular or nonspecific mitogenic stimuli. Blood. May 15, 2002;99(10):3838-43.
Diduch et al., Two cell lines from bone marrow that differ in terms of collagen synthesis, osteogenic characteristics, and matrix mineralization. J Bone Joint Surg Am. Jan. 1993;75(1):92-105.
Dieu et al., Selective recruitment of immature and mature dendritic cells by distinct chemokines expressed in different anatomic sites. J Exp Med. Jul. 20, 1998;188(2):373-86.
Diridollou et al., Skin ageing: changes of physical properties of human skin in vivo. Int J Cosmet Sci. Dec. 2001;23(6):353-62.
Discher et al., Tissue cells feel and respond to the stiffness of their substrate. Science. Nov. 18, 2005;310(5751):1139-43.
Disis et al., Granulocyte-macrophage colony-stimulating factor: an effective adjuvant for protein and peptide-based vaccines. Blood. Jul. 1, 1996;88(1):202-10.
Doan et al., Antigens and Receptors. Immunology. Wolters Kluwer/Lippincott Williams & Wilsons, Philadelphia. 2008:11-23.
Doan et al., Subcellular localization of a sporulation membrane protein is achieved through a network of interactions along and across the septum. Mol Microbiol. Mar. 2005;55(6):1767-81.
Donati et al., New hypothesis on the role of alternating sequences in calcium-alginate gels. Biomacromolecules. Mar.-Apr. 2005;6(2):1031-40.
Dor et al., Making vascular networks in the adult: branching morphogenesis without a roadmap. Trends Cell Biol. Mar. 2003;13(3):131-6.
Douay et al., Ex vivo production of human red blood cells from hematopoietic stem cells: what is the future in transfusion? Transfus Med Rev. Apr. 2007;21(2):91-100.
Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-43.
Dranoff, Cytokines in cancer pathogenesis and cancer therapy. Nat Rev Cancer. Jan. 2004;4(1):11-22.

(56) References Cited

OTHER PUBLICATIONS

Dranoff, GM-CSF-based cancer vaccines. Immunol Rev. Oct. 2002;188:147-54.
Dudley et al. Adoptive cell transfer therapy following non-myeloablative but lymphodepleting chemotherapy for the treatment of patients with refractory metastatic melanoma. J Clin Oncol. Apr. 1, 2005;23(10):2346-57.
Dufort et al., Balancing forces: architectural control of mechanotransduction. Nat Rev Mol Cell Biol. May 2011;12(5):308-19.
Dupont et al., Role of YAP/TAZ in mechanotransduction. Nature. Jun. 8, 2011;474(7350):179-83.
Edwards et al., Evaluation of biomechanical properties of human skin. Clin Dermatol. Jul.-Aug. 1995;13(4):375-80.
Egholm et al., Peptide Nucleic Acids (PNA). Oligonucleotide Analogues with an Achiral Peptide Backbone. J Am Chem Soc. 1992;114(5):1895-1897.
Egholm et al., PNA hybridizes to complementary oligonucleotides obeying the Watson-Crick hydrogen-bonding rules. Nature. Oct. 7, 1993;365(6446):566-8.
Ehrbar et al., Endothelial cell proliferation and progenitor maturation by fibrin-bound VEGF variants with differential susceptibilities to local cellular activity. J Control Release. Jan. 3, 2005;101(1-3):93-109.
Eiselt et al., Porous carriers for biomedical applications based on alginate hydrogels. Biomaterials. Oct. 2000;21(19):1921-7.
El-Backly et al., Regeneration of dentine/pulp-like tissue using a dental pulp stem cell/poly(lactic-co-glycolic) acid scaffold construct in New Zealand white rabbits. Aust Endod J. Aug. 2008;34(2):52-67.
Eldar et al., Elucidating mechanisms underlying robustness of morphogen gradients. Curr Opin Genet Dev. Aug. 2004;14(4):435-9.
Eldar et al., Robustness of the BMP morphogen gradient in *Drosophila* embryonic patterning. Nature. Sep. 19, 2002;419(6904):304-8.
Eldar et al., Self-enhanced ligand degradation underlies robustness of morphogen gradients. Dev Cell. Oct. 2003;5(4):635-46.
Eming et al., Inflammation in wound repair: molecular and cellular mechanisms. J Invest Dermatol. Mar. 2007;127(3):514-25.
Engler et al., Matrix elasticity directs stem cell lineage specification. Cell. Aug. 25, 2006;126(4):677-89.
Engler et al., Microtissue elasticity: measurements by atomic force microscopy and its influence on cell differentiation. Methods Cell Biol. 2007;83:521-45.
Engler et al., Substrate compliance versus ligand density in cell on gel responses. Biophys J. Jan. 2004;86(1 Pt 1):617-28.
Ennett et al., Temporally regulated delivery of VEGF in vitro and in vivo. J Biomed Mater Res A. Oct. 2006;79(1):176-84.
Exposito et al., The fibrillar collagen family. Int J Mol Sci. Jan. 28, 2010;11(2):407-26.
Faissner et al., Boundaries and inhibitory molecules in developing neural tissues. Glia. Apr. 1995;13(4):233-54.
Falanga, Wound healing and its impairment in the diabetic foot. Lancet. Nov. 12, 2005;366(9498):1736-43.
Falsey et al., Peptide and small molecule microarray for high throughput cell adhesion and functional assays. Bioconjug Chem. May-Jun. 2001;12(3):346-53.
Farrar et al., T helper subset development: roles of instruction, selection, and transcription. J Clin Invest. Feb. 2002;109(4):431-5.
Fauquemberque et al., HLA-A*0201-restricted CEA-derived peptide CAP1 is not a suitable target for T-cell-based immunotherapy. J Immunother. May 2010;33(4):402-13.
Ferrara et al., Angiogenesis as a therapeutic target. Nature. Dec. 15, 2005;438(7070):967-74.
Ferrara et al., Discovery and development of bevacizumab, an anti-VEGF antibody for treating cancer. Nat Rev Drug Discov. May 2004;3(5):391-400.
Fischer et al., A brilliant monomeric red fluorescent protein to visualize cytoskeleton dynamics in Dictyostelium. FEBS Lett. Nov. 5, 2004;577(1-2):227-32.

Fischer et al., Visualizing cytoskeleton dynamics in mammalian cells using a humanized variant of monomeric red fluorescent protein. FEBS Lett. May 1, 2006;580(10):2495-502.
Fisher et al., The study of protein mechanics with the atomic force microscope. Trends Biochem Sci. Oct. 1999;24(10):379-84.
Folkman, Angiogenesis. Annu Rev Med. 2006;57:1-18.
Fonseca et al., Capitalizing on the immunogenicity of dying tumor cells. Clin Cancer Res. Mar. 15, 2008;14(6):1603-8.
Fontaine et al., Surgical treatment of peripheral circulation disorders. Helv Chir Acta. Dec. 1954;21(5-6):499-533.
Fox, Management of worsening multiple sclerosis with mitoxantrone: a review. Clin Ther. Apr. 2006;28(4):461-74.
Fransen et al., Local immunomodulation for cancer therapy: Providing treatment where needed. Oncoimmunology. Nov. 1, 2013;2(11):e26493.
Friedenstein et al., Fibroblast precursors in normal and irradiated mouse hematopoietic organs. Exp Hematol. Sep. 1976;4(5):267-74.
Friedrich et al., Promoter traps in embryonic stem cells: a genetic screen to identify and mutate developmental genes in mice. Genes Dev. Sep. 1991;5(9):1513-23.
Fukushima et al., The use of an antifibrosis agent to improve muscle recovery after laceration. Am J Sports Med. Jul.-Aug. 2001;29(4):394-402.
Gamvrellis et al., Vaccines that facilitate antigen entry into dendritic cells. Immunol Cell Biol. Oct. 2004;82(5):506-16.
Gardel et al., Traction stress in focal adhesions correlates biphasically with actin retrograde flow speed. J Cell Biol. Dec. 15, 2008;183(6):999-1005.
Gasic et al., Removal and regeneration of the cell coating in tumour cells. Nature. Oct. 13, 1962;196:170.
Gauthier et al., Temporary increase in plasma membrane tension coordinates the activation of exocytosis and contraction during cell spreading. Proc Natl Acad Sci U S A. Aug. 30, 2011;108(35):14467-72.
Geerligs et al., Linear viscoelastic behavior of subcutaneous adipose tissue. Biorheology. 2008;45(6):677-88.
GenBank Accession No. 000082.2, May 10, 2014.
GenBank Accession No. 000091.4, May 10, 2014.
GenBank Accession No. 000230.2, Dec. 17, 2012.
GenBank Accession No. 000514.3, Aug. 19, 2012.
GenBank Accession No. 000572.2, May 18, 2014.
GenBank Accession No. 000601.4, Nov. 25, 2012.
GenBank Accession No. 000614.3, Sep. 9, 2012.
GenBank Accession No. 000629.3, May 4, 2014.
GenBank Accession No. 000638.3, May 4, 2014.
GenBank Accession No. 000660.4, Dec. 9, 2012.
GenBank Accession No. 000749.2, May 4, 2014.
GenBank Accession No. 000758.3, May 4, 2014.
GenBank Accession No. 000800.3, Mar. 4, 2012.
GenBank Accession No. 000876.3, Apr. 13, 2014.
GenBank Accession No. 000885.4, Apr. 13, 2014.
GenBank Accession No. 000954.1, Jun. 13, 2014.
GenBank Accession No. 000963.3, Jun. 13, 2014.
GenBank Accession No. 001001522.1, May 18, 2014.
GenBank Accession No. 001096124.1, Dec. 16, 2012.
GenBank Accession No. 001102654.1, Dec. 16, 2012.
GenBank Accession No. 001111283.1, Dec. 9, 2012.
GenBank Accession No. 001171630.1, Dec. 9, 2012.
GenBank Accession No. 001202.3, Nov. 18, 2012.
GenBank Accession No. 001836.2, May 3, 2014.
GenBank Accession No. 001845.4, May 3, 2014.
GenBank Accession No. 001892.1, May 18, 2014.
GenBank Accession No. 001901.2, May 18, 2014.
GenBank Accession No. 002010.2, Dec. 9, 2012.
GenBank Accession No. 002421.3, May 11, 2014.
GenBank Accession No. 002506.2, Dec. 9, 2012.
GenBank Accession No. 002632.4, May 4, 2011.
GenBank Accession No. 002973.1, May 3, 2014.
GenBank Accession No. 002982.3, May 3, 2014.
GenBank Accession No. 003236.2, Aug. 21, 2011.
GenBank Accession No. 003239.2, Feb. 18, 2014.
GenBank Accession No. 003254.2, Jan. 5, 2013.
GenBank Accession No. 003255.2, Jan. 6, 2013.

(56) References Cited

OTHER PUBLICATIONS

GenBank Accession No. 003259.2, Nov. 25, 2012.
GenBank Accession No. 003263.3, Jan. 5, 2013.
GenBank Accession No. 003264.3, Jan. 6, 2013.
GenBank Accession No. 003268.5, Nov. 25, 2012.
GenBank Accession No. 003368.1, May 5, 2014.
GenBank Accession No. 003377.4, May 5, 2014.
GenBank Accession No. 003383.2, May 5, 2014.
GenBank Accession No. 003392.4, May 5, 2014.
GenBank Accession No. 004460.1, May 25, 2014.
GenBank Accession No. 004469.4, May 25, 2014.
GenBank Accession No. 005420.1, May 11, 2014.
GenBank Accession No. 005429.3, Mar. 31, 2014.
GenBank Accession No. 006059.2, Oct. 28, 2012.
GenBank Accession No. 006068.4, Oct. 28, 2012.
GenBank Accession No. 015719.3, Feb. 26, 2014.
GenBank Accession No. 016562.3, Jan. 6, 2013.
GenBank Accession No. 030956.3, Oct. 28, 2012.
GenBank Accession No. 033023.4, Nov. 18, 2012.
GenBank Accession No. 056534.2, Feb. 26, 2014.
GenBank Accession No. 057646.1, Jan. 6, 2013.
GenBank Accession No. 112218.2, Oct. 28, 2012.
GenBank Accession No. 138554.4, Dec. 29, 2012.
GenBank Accession No. 138636.4, Dec. 23, 2012.
GenBank Accession No. 170731.4, Dec. 9, 2012.
GenBank Accession No. 205819.3, Dec. 6, 2012.
GenBank Accession No. 205820.1, Jan. 5, 2013.
GenBank Accession No. 205823.2, Jan. 6, 2013.
GenBank Accession No. 570912.2, Nov. 18, 2012.
GenBank Accession No. 612564.1, Dec. 29, 2012.
GenBank Accession No. 619542.1, Dec. 23, 2012.
GenBank Accession No. 991388.2, Dec. 6, 2012.
GenBank Accession No. 991389.1, Jan. 5, 2013.
GenBank Accession No. 991392.1, Jan. 6, 2013.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56738.1, Dec. 7, 1994.
GenBank Accession No. AAA60022.1, Jan. 7, 1995.
GenBank Accession No. AAA60552.1, Nov. 24, 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. AAH94877.1, May 20, 2005.
GenBank Accession No. AAI44040, Mar. 18, 2009.
GenBank Accession No. ABC86910, Jan. 3, 2011.
GenBank Accession No. AE022039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. DQ103757.1, Jul. 25, 2005.
GenBank Accession No. EF064765.1, Nov. 13, 2006.
GenBank Accession No. EU826563.1, Jul. 23, 2008.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. P49771.1, Jan. 9, 2013.
GenBank Accession No. U76381.2, Jul. 12, 1999.
Genes et al., Effect of substrate mechanics on chondrocyte adhesion to modified alginate surfaces. Arch Biochem Biophys. Feb. 15, 2004;422(2):161-7.
Gerhardt et al., VEGF guides angiogenic sprouting utilizing endothelial tip cell filopodia. J Cell Biol. Jun. 23, 2003;161(6):1163-77.
Gilboa, DC-based cancer vaccines. J Clin Invest. May 2007;117(5):1195-203.
Glasbey et al., Image Analysis and Three-Dimensional Modelling of Pores in Soil Aggregates. Eur J Soil Sci. Sep. 1991;42(3):479-486.
Gnjatic et al., Toll-like receptor agonists: are they good adjuvants? Cancer J. Jul.-Aug. 2010;16(4):382-91.
Godbey et al. Tracking the intracellular path of poly(ethylenimine)/DNA complexes for gene delivery. Proc Natl Acad Sci U S A. Apr. 27, 1999;96(9):5177-81.
Godbey et al., Size matters: molecular weight affects theefficiency of poly(ethylenimine) as a gene delivery vehicle. J Biomed Mater Res. Jun. 5, 1999;45(3):268-75.
Gospodarowicz et al., Effect of fibroblast growth factor on the division and fusion of bovine myoblasts. J Cell Biol. Aug. 1976;70(2 pt 1):395-405.
Graessley, Entangled Linear, Branched and Network Polymer Systems—Molecular Theories. Adv Poly Sci. 1982;47:67-117.
Griffith et al., Tissue engineering—current challenges and expanding opportunities. Science. Feb. 8, 2002;295(5557):1009-14.
Grimmer et al., Tracheal reconstruction using tissue-engineered cartilage. Arch Otolaryngol Head Neck Surg. Oct. 2004;130(10):1191-6.
Gros et al., A common somitic origin for embryonic muscle progenitors and satellite cells. Nature. Jun. 16, 2005;435(7044):954-8.
Guillaume et al., Two abundant proteasome subtypes that uniquely process some antigens presented by HLA class I molecules. Proc Natl Acad Sci U S A. Oct. 26, 2010;107(43):18599-604.
Gullberg et al., Extracellular matrix and its receptors during development. Int J Dev Biol. Oct. 1995;39(5):845-54.
Guo et al., Droplet microfluidics for high-throughput biological assays. Lab Chip. Jun. 21, 2012;12(12):2146-55.
Gupta et al., Magnetically controlled targeted micro-carrier systems. Life Sci. 1989;44(3):175-86.
Gurkan et al., The mechanical environment of bone marrow: a review. Ann Biomed Eng. Dec. 2008;36(12):1978-91.
Gussoni et al., Dystrophin expression in the mdx mouse restored by stem cell transplantation. Nature. Sep. 23, 1999;401(6751):390-4.
Halim et al., Biologic and synthetic skin substitutes: An overview. Indian J Plast Surg. Sep. 2010;43(Suppl):S23-8.
Hamby et al., Small molecule inhibitors of tumor-promoted angiogenesis, including protein tyrosine kinase inhibitors. Pharmacol Ther. May-Jun. 1999;82(2-3):169-93.
Hamdy et al., Targeting dendritic cells with nano-particulate PLGA cancer vaccine formulations. Adv Drug Deliv Rev. Sep. 10, 2011;63(10-11):943-55.
Hamilton et al., GM-CSF Biology. Growth Factors. Dec. 2004;22(4):225-31.
Hamilton, GM-CSF in inflammation and autoimmunity. Trends Immunol. Aug. 2002;23(8):403-8.
Hanada, Efficacy of rehabilitative therapy in regional musculoskeletal conditions. Best Pract Res Clin Rheumatol. Feb. 2003;17(1):151-66.
Hansen et al., Comparison of clinical grade type 1 polarized and standard matured dendritic cells for cancer immunotherapy. Vaccine. Jan. 11, 2013;31(4):639-46.
Hansen et al., Integrin binding and cell spreading on extracellular matrix act at different points in the cell cycle to promote hepatocyte growth. Mol Biol Cell. Sep. 1994;5(9):967-75.
Harris et al., Open pore biodegradable matrices formed with gas foaming. J Biomed Mater Res. Dec. 5, 1998;42(3):396-402.

(56) References Cited

OTHER PUBLICATIONS

Harris, Classification, Diagnostic Criteria, and Screening for Diabetes. Diabetes in America. NIH Publication No. 95-1468. Chapter 2. (1995):15-36.
Harrison, What is the status of reaction-diffusion theory thirty-four years after turing? J Theor Biol. Apr. 21, 1987;125(4):369-84.
Hartgerink et al., Peptide-amphiphile nanofibers: a versatile scaffold for the preparation of self-assembling materials. Proc Natl Acad Sci U S A. Apr. 16, 2002;99(8):5133-8.
Hartmann et al., CpG DNA: a potent signal for growth, activation, and maturation of human dendritic cells. Proc Natl Acad Sci U S A. Aug. 3, 1999;96(16):9305-10.
Hashimoto et al., Development of alginate wound dressings linked with hybrid peptides derived from laminin and elastin. Biomaterials. Mar.-Apr. 2004;25(7-8):1407-14.
Hawke et al., Myogenic satellite cells: physiology to molecular biology. J Appl Physiol (1985). Aug. 2001;91(2):534-51.
Heath, Cells for tissue engineering. Trends Biotechnol. Jan. 2000;18(1):17-9.
Helm et al., Synergy between interstitial flow and VEGF directs capillary morphogenesis in vitro through a gradient amplification mechanism. Proc Natl Acad Sci U S A. Nov. 1, 2005;102(44):15779-84.
Henry et al., VIVA Investigators. The VIVA trial: Vascular endothelial growth factor in Ischemia for Vascular Angiogenesis. Circulation. Mar. 18, 2003;107(10):1359-65.
Hermanson, Bioconjugate Techniques. New York: Academic Press. (1996):152-185.
Heslop et al., Transplanted primary neonatal myoblasts can give rise to functional satellite cells as identified using the Myf5nlacZl+ mouse. Gene Ther. May 2001;8(10):778-83.
Hildner et al., Batf3 deficiency reveals a critical role for CD8alpha+ dendritic cells in cytotoxic T cell immunity. Science. Nov. 14, 2008;322(5904):1097-100.
Hill et al., Designing scaffolds to enhance transplanted myoblast survival and migration. Tissue Eng. May 2006;12(5):1295-304.
Hill et al., Muscle satellite (stem) cell activation during local tissue injury and repair. J Anat. Jul. 2003;203(1):89-99.
Hill, Macroporous Scaffold Architecture, Peptide, HGF/FGF and Myoblast Incorporation Enhance Myogenesis. IADR/AADR/CADR 83rd General Session. Mar. 9-12, 2005. Poster #2829.
Hirano et al., Peptide and Protein Presenting Materials for Tissue Engineering. Adv Mat. Jan. 16, 2004;16(1):17-25.
Hodge-Dufour et al., Inhibition of interferon gamma induced interleukin 12 production: a potential mechanism for the anti-inflammatory activities of tumor necrosis factor. Proc Natl Acad Sci U S A. Nov. 10, 1998;95(23):13806-11.
Hodi et al., Immunologic and clinical effects of antibody blockade of cytotoxic T lymphocyte-associated antigen 4 in previously vaccinated cancer patients. Proc Natl Acad Sci U S A. Feb. 26, 2008;105(8):3005-10.
Holland et al., Transforming growth factor-beta 1 release from oligo(poly(ethylene glycol) fumarate) hydrogels in conditions that model the cartilage wound healing environment. J Control Release. Jan. 8, 2004;94(1):101-14.
Horsley et al., IL-4 acts as a myoblast recruitment factor during mammalian muscle growth. Cell. May 16, 2003;113(4):483-94.
Hsiong et al., Differentiation stage alters matrix control of stem cells. J Biomed Mater Res A. Apr. 2008;85(1):145-56.
Huang et al., Fabrication and in vitro Testing of Polymeric Delivery Systems for Condensed DNA. J Biomed Mater Res. 2003;67:1384-1392.
Huang et al., Long-Term In Vivo Gene Expression via Delivery of PEI-DNA Condensates From Porous Polymer Scaffolds. Hum Gene Ther. 2005;16(5):609-617.
Hubbell et al., Materials Engineering for Immunomodulation. Nature. 2009;462:449-460.
Hubbell, Biomaterials in tissue engineering. Biotechnology (N Y). Jun. 1995;13(6):565-76.
Huebsch et al., Harnessing traction-mediated manipulation of the cell/matrix interface to control stem-cell fate. Nat Mater. Jun. 2010;9(6):518-26.
Humphries et al., Integrin ligands at a glance. J Cell Sci. Oct. 1, 2006;119(Pt 19):3901-3.
Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Hutson et al., Synthesis and characterization of tunable poly(ethylene glycol): gelatin methacrylate composite hydrogels. Tissue Eng Part A. Jul. 2011;17(13-14):1713-23.
Hwang et al., Fabrication of three-dimensional porous cell-laden hydrogel for tissue engineering. Biofabrication. Sep. 2010;2(3):035003.
Ihnat et al., Hypothesis: the 'metabolic memory', the new challenge of diabetes. Diabet Med. Jun. 2007;24(6):582-6.
Il et al., A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling. Mol Pharmacol. Apr. 2006;69(4):1288-95.
Isern et al., Self-renewing human bone marrow mesenspheres promote hematopoietic stem cell expansion. Cell Rep. May 30, 2013;3(5):1714-24.
Ishihara et al., Roles of bradykinin in vascular permeability and angiogenesis in solid tumor. Int Immunopharmacol. Mar. 2002;2(4):499-509.
Iwamoto et al., Preparation of an Ionic Polymer Gel Microactuator and Measurement of its Periodic Motions. Nippon Kagaku Kaishi. 1997;9:609-614.
Jain, Molecular Regeneration of Vessel Maturation. Nat Med. Jun. 1, 2003;9:685-693.
Jain, The manufacturing techniques of various drug loaded biodegradable poly(lactide-co-glycolide) (PLGA) devices. Biomaterials. Dec. 2000;21(23):2475-90.
Jankovic et al., In the absence of IL-12, CD4(+) T cell responses to intracellular pathogens fail to default to a Th2 pattern and are host protective in an IL-10(−/−) setting. Immunity. Mar. 2002;16(3):429-39.
Janmey et al., From tissue mechanics to transcription factors. Differentiation. Oct. 2013;86(3):112-20.
Jego et al., Plasmacytoid dendritic cells induce plasma cell differentiation through type I interferon and interleukin 6. Immunity. Aug. 2003;19(2):225-34.
Jiang et al. Two-piconewton slip bond between fibronectin and the cytoskeleton depends on talin. Nature. Jul. 17, 2003;424(6946):334-7.
Jiang et al., Self-organization of periodic patterns by dissociated feather mesenchymal cells and the regulation of size, number and spacing of primordia. Development. Nov. 1999;126(22):4997-5009.
Jinushi et al., Enhancing the clinical activity of granulocyte-macrophage colony-stimulating factor-secreting tumor cell vaccines. Immunol Rev. Apr. 2008;222:287-98.
Jinushi et al., MFG-E8-mediated uptake of apoptotic cells by APCs links the pro- and antiinflammatory activities of GM-CSF. J Clin Invest. Jul. 2007;117(7):1902-13.
Johnson et al., Activation of skeletal muscle satellite cells and the role of fibroblast growth factor receptors. Exp Cell Res. Aug. 1995;219(2):449-53.
Jokinen et al., Integrin-mediated cell adhesion to type I collagen fibrils. J Biol Chem. Jul. 23, 2004;279(30):31956-63.
Jugdutt et al., Aging and defective healing, adverse remodeling, and blunted post-conditioning in the reperfused wounded heart. J Am Coll Cardiol. Apr. 8, 2008;51(14):1399-403.
Juntanon et al., Electrically controlled release of sulfosalicylic acid from crosslinked poly(vinyl alcohol) hydrogel. Int J Pharm. May 22, 2008;356(1-2):1-11.
Kang et al., Effect of Porous Structure on the Degradation of Freeze-Dried Gelatin Hydrogels. J Bioact Compat Poly. Jul. 1, 1999;14(4):331-343.
Kanzler et al., Therapeutic targeting of innate immunity with Toll-like receptor agonists and antagonists. Nat Med. May 2007;13(5):552-9.

(56) References Cited

OTHER PUBLICATIONS

Katayama et al., Integrated analysis of the genome and the transcriptome by FANTOM. Brief Bioinform. Sep. 2004;5(3):249-58.
Kawai et al., Innate immune recognition of viral infection. Nat Immunol. Feb. 2006;7(2):131-7.
Kawashima et al., Pulmonary delivery of insulin with nebulized DL-lactide/glycolide copolymer (PLGA) nanospheres to prolong hypoglycemic effect. J Control Release. Nov. 1, 1999;62(1-2):279-87.
Kearney et al., Macroscale delivery systems for molecular and cellular payloads. Nat Mater. Nov. 2013;12(11):1004-17.
Kennedy et al., Rapid and extensive collapse from electrically responsive macroporous hydrogels. Adv Healthc Mater. Apr. 2014;3(4):500-7.
Khetan et al., Degradation-mediated cellular traction directs stem cell fate in covalently crosslinked three-dimensional hydrogels. Nat Mater. May 2013;12(5):458-65.
Khownium et al., Novel endotoxin-sequestering compounds with terephthalaldehyde-bis-guanylhydrazone scaffolds. Bioorg Med Chem Lett. Mar. 1, 2006;16(5):1305-8.
Kim et al., An overview of cartilage tissue engineering. Yonsei Med J. Dec. 2000;41(6):766-73.
Kim et al., Multifunctional capsule-in-capsules for immunoprotection and trimodal imaging. Angew Chem Int Ed Engl. Mar. 1, 2011;50(10):2317-21.
Kim et al., The effect of VEGF on the myogenic differentiation of adipose tissue derived stem cells within thermosensitive hydrogel matrices. Biomaterials. Feb. 2010;31(6):1213-8.
Kinoshita et al., Successive injections in mdx mice of myoblasts grown with bFGF. Neuromuscul Disord. May 1996;6(3):187-93.
Kisak et al. The vesosome—a multicompartment drug delivery vehicle. Curr Med Chem. Jan. 2004;11(2):199-219.
Klebanoff et al., CD8+ T-cell memory in tumor immunology and immunotherapy. Immunol Rev. Jun. 2006;21 1:214-24.
Klein et al., Cell-Cycle Control by Physiological Matrix Elasticity and In Viivo Tissue Stiffening. Curr Biol. Sep. 29, 2009;19:1511-1518.
Klinman, Immunotherapeutic uses of CpG oligodeoxynucleotides. Nat Rev Immunol. Apr. 2004;4(4):249-58.
Kohane, Microparticles and nanoparticles for drug delivery. Biotechnol Bioeng. Feb. 1, 2007 ;96(2):203-9.
Kondo et al., A reaction-diffusion wave on the skin of the marine angelfish Pomacanthus. Nature. Aug. 31, 1995;376(6543):765-8.
Kong et al., Controlling Degradation of Hydrogels via the Size of Cross-Linked Junctions. Adv Mater. Nov. 30, 2004;16(21):1917-1921.
Kong et al., Controlling rigidity and degradation of alginate hydrogels via molecular weight distribution. Biomacromolecules. Sep.-Oct. 2004;5(5):1720-7.
Kong et al., Decoupling the Dependence of Rheological/Mechanical Properties of Hydrogels from Solids Concentration. Polymer. 2002;43(23):6239-6246.
Kong et al., Design of biodegradable hydrogel for the local and sustained delivery of angiogenic plasmid DNA. Pharm Res. May 2008;25(5):1230-8.
Kong et al., Designing alginate hydrogels to maintain viability of immobilized cells. Biomaterials. Oct. 2003;24(22):4023-9.
Kong et al., FRET measurements of cell-traction forces and nanoscale clustering of adhesion ligands varied by substrate stiffness. Proc Natl Acad Sci U S A. Mar. 22, 2005;102(12):4300-5.
Kong et al., Non-viral gene delivery regulated by stiffness of cell adhesion substrates. Nat Mater. Jun. 2005;4(6):460-4.
Kratky et al., Direct activation of antigen-presenting cells is required for CD8+ T-cell priming and tumor vaccination. Proc Natl Acad Sci U S A. Oct. 18, 2011;108(42):17414-9.
Krieg, Development of TLR9 agonists for cancer therapy. J Clin Invest. May 2007;117(5):1184-94.
Krishnamachari et al., PLGA Microparticles that Co-Deliver Antigen and Toll Like Receptor Ligand Adjuvants for Applications in Cancer Immunotherapy. AAPS Pharmaceutica. Nov. 11, 2009. Web. Mar. 1, 2013. http://abstracts.aapspharmaceutica.com/ExpoAAPS09/CC/forms/attendee/index-.aspx?content=sessionInfo&sessionId=2716.
Kumamoto et al., Induction of tumor-specific protective immunity by in situ Langerhans cell vaccine. Nat Biotechnol. Jan. 2002;20(1):64-9.
Kumar et al., Toll-like receptors and innate immunity. Biochem Biophys Res Commun. Oct. 30, 2009;388(4):621-5.
Kurts et al., CD8 T cell ignorance or tolerance to islet antigens depends on antigen dose. Proc Natl Acad Sci U S A. Oct. 26, 1999;96(22):12703-7.
Kuwahara et al., Cell delivery using an injectable and adhesive transglutaminase-gelatin gel. Tissue Eng Part C Methods. Aug. 2010;16(4):609-18.
Kwon et al., Electrically erodible polymer gel for controlled release of drugs. Nature. Nov. 28, 1991;354(6351):291-3.
Kwon et al., In vivo targeting of dendritic cells for activation of cellular immunity using vaccine carriers based on pH-responsive microparticles. Proc Natl Acad Sci U S A. Dec. 20, 2005;102(51):18264-8.
Langenkamp et al., Kinetics of dendritic cell activation: impact on priming of TH1, TH2 and nonpolarized T cells. Nat Immunol. Oct. 2000;1(4):311-6.
Langer et al., Tissue engineering. Science. May 14, 1993;260(5110):920-6.
Lanzavecchia et al., Regulation of T cell immunity by dendritic cells. Cell. Aug. 10, 2001;106(3):263-6.
Lao et al., Magnetic and hydrogel composite materials for hyperthermia applications. J Mater Sci Mater Med. Oct. 2004;15(10):1061-4.
Latorre et al., Applications of magnetic nanoparticles in medicine: magnetic fluid hyperthermia. P R Health Sci J. Sep. 2009;28(3):227-38.
Lauterbach et al., Mouse CD8alpha+ DCs and human BDCA3+ DCs are major producers of IFN-lambda in response to poly IC. J Exp Med. Nov. 22, 2010;207(12):2703-17.
Leach et al., Coating of VEGF-releasing scaffolds with bioactive glass for angiogenesis and bone regeneration. Biomaterials. Jun. 2006; 27(17):3249-55.
Lee et al., Engineering liver tissue spheroids with inverted colloidal crystal scaffolds. Biomaterials. Sep. 2009;30(27):4687-94.
Lee et al., Hydrogel Formation via Vell Crosslinking. Advanced Materials. Nov. 2003;15(21):1828-1832.
Lee et al., Hydrogels for tissue engineering. Chem Rev. Jul. 2001;101(7):1869-79.
Lee et al., Intravenous hMSCs improve myocardial infarction in mice because cells embolized in lung are activated to secrete the anti-inflammatory protein TSG-6. Cell Stem Cell. Jul. 2, 2009;5(1):54-63.
Lefaucheur et al., The cellular events of injured muscle regeneration depend on the nature of the injury. Neuromuscul Disord. Nov. 1995;5(6):501-9.
Lele et al., Investigating complexity of protein-protein interactions in focal adhesions. Biochem Biophys Res Commun. May 9, 2008;369(3):929-34.
Lensch et al., Scientific and clinical opportunities for modeling blood disorders with embryonic stem cells. Blood. Apr. 1, 2006;107(7):2605-12.
Leor et al., Cells, scaffolds, and molecules for myocardial tissue engineering. Pharmacol Ther. Feb. 2005;105(2):151-63.
Leshem et al., Hepatocyte growth factor (HGF) inhibits skeletal muscle cell differentiation: a role for the bHLH protein twist and the cdk inhibitor p27. J Cell Physiol. Jul. 2000;184(1):101-9.
Letsinger et al., Phosphoramidate analogs of oligonucleotides. J Org Chem. Nov. 1970;35(11):3800-3.
Levental et al., Soft Biological Materials and their Impact on Cell Function. Soft Matter. 2007;3:299-306.
Li et al., Effect of growth factors and extracellular matrix materials on the proliferation and differentiation of microencapsulated myoblasts. J Biomater Sci Polym Ed. 2003;14(6):533-49.
Li et al., Effects of Three-Dimensional Scaffolds on Cell Organization and Tissue Development. Biotechnology and Bioprocess Engineering. Oct. 2001;6(5):311-325.

(56) References Cited

OTHER PUBLICATIONS

Li et al., Purified hybrid cells from dendritic cell and tumor cell fusions are superior activators of antitumor immunity. Cancer Immunol Immunother. Nov. 2001;50(9):456-62.
Li, TNF-alpha is a mitogen in skeletal muscle. Am J Physiol Cell Physiol. Aug. 2003;285(2):C370-6.
Lin et al., Transdermal regulation of vascular network bioengineering using a photopolymerizable methacrylated gelatin hydrogel. Biomaterials. Sep. 2013;34(28):6785-96.
Lipton et al., Developmental fate of skeletal muscle satellite cells. Science. Sep. 21, 1979;205(4412):1292-4.
Liu et al., Heterobifunctional poly(ethylene glycol)-tethered bone morphogenetic protein-2-stimulated bone marrow mesenchymal stromal cell differentiation and osteogenesis. Tissue Eng. May 2007;13(5):1113-24.
Liu et al., Immunostimulatory CpG oligodeoxynucleotides enhance the immune response to vaccine strategies involving granulocyte-macrophage colony-stimulating factor. Blood. Nov. 15, 1998;92(10):3730-6.
Liu et al., Nanostructured materials designed for cell binding and transduction. Biomacromolecules. 2001 Summer;2(2):362-8.
Liu et al., On the viscoelastic character of liver tissue: experiments and modelling of the linear behaviour. Biorheology. 2000;37(3):191-201.
Liu, Dendritic cell subsets and lineages, and their functions in innate and adaptive immunity. Cell. Aug. 10, 2001;106(3):259-62.
Lo et al., Cell movement is guided by the rigidity of the substrate. Biophys J. Jul. 2000;79(1):144-52.
Lodish et al., Collagen: The Fibrous Proteins of the Matrix. Molecular Cell Biology. W.H. Freeman, New York. 2000;Section 22.3:979-985.
Lopez et al., Magnetic Applications of Polymer Gels. Macromol Symp. 2001;166(1):173-178.
Lu et al., Muscle-derived stem cells seeded into acellular scaffolds develop calcium-dependent contractile activity that is modulated by nicotinic receptors. Urology. Jun. 2003;61(6):1285-91.
Lubeck, The costs of musculoskeletal disease: health needs assessment and health economics. Best Pract Res Clin Rheumatol. Jun. 2003;17(3):529-39.
Ludewig et al., Immunotherapy with dendritic cells directed against tumor antigens shared with normal host cells results in severe autoimmune disease. J Exp Med. Mar. 6, 2000;191(5):795-804.
Lumelsky et al., Differentiation of embryonic stem cells to insulin-secreting structures similar to pancreatic islets. Science. May 18, 2001;292(5520):1389-94.
Lutolf et al., Repair of bone defects using synthetic mimetics of collagenous extracellular matrices. Nat Biotechnol. May 2003;21(5):513-8.
Mach et al., Differences in dendritic cells stimulated in vivo by tumors engineered to secrete granulocyte-macrophage colony-stimulating factor or Flt3-ligand. Cancer Res. Jun. 15, 2000;60(12):3239-46.
Magram et al., IL-12-deficient mice are defective but not devoid of type 1 cytokine responses. Ann N Y Acad Sci. Oct. 31, 1996;795:60-70.
Maini, Spatial and spatio-temporal patterns in a cell-haptotaxis model. J Math Biol. 1989;27(5):507-22.
Majeti et al., Identification of a hierarchy of multipotent hematopoietic progenitors in human cord blood. Cell Stem Cell. Dec. 13, 2007;1(6):635-45.
Maley et al., Extracellular matrix, growth factors,genetics: their influence on cell proliferation and myotube formation in primary cultures of adult mouse skeletal muscle. Exp Cell Res. Jul. 1995;219(1):169-79.
Malhotra et al., Use of an oncolytic virus secreting GM-CSF as combined oncolytic and immunotherapy for treatment of colorectal and hepatic adenocarcinomas. Surgery. Apr. 2007;141(4):520-9.
Malmqvist, Biospecific interaction analysis using biosensor technology. Nature. Jan. 14, 1993;361(6408):186-7.

Mammoto et al., Mechanical control of tissue and organ development. Development. May 2010;137(9):1407-20.
Manavski et al., Vascular niche controls organ regeneration. Circ Res. Mar. 28, 2014;114(7):1077-9.
Mansoor et al., Engineering T cells for cancer therapy. Br J Cancer. Nov. 14, 2005;93(10):1085-91.
Martinsen et al., Alginate as immobilization material: I. Correlation between chemical and physical properties of alginate gel beads. Biotechnol Bioeng. Jan. 5, 1989;33(1):79-89.
Marui et al., Simultaneous application of basic fibroblast growth factor and hepatocyte growth factor to enhance the blood vessels formation. J Vasc Surg. Jan. 2005;41(1):82-90.
Masedunskas et al., Role for the actomyosin complex in regulated exocytosis revealed by intravital microscopy. Proc Natl Acad Sci U S A. Aug. 16, 2011;108(33):13552-7.
Massia et al., An RGD spacing of 440 nm is sufficient for integrin alpha V beta 3-mediated fibroblast spreading and 140 nm for focal contact and stress fiber formation. J Cell Biol. Sep. 1991;114(5):1089-100.
Matthew et al., Subperiosteal behaviour of alginate and cellulose wound dressing materials. Biomaterials. Mar. 1995;16(4):275-8.
McDonald et al., Early fracture callus displays smooth muscle-like viscoelastic properties ex vivo: implications for fracture healing. J Orthop Res. Nov. 2009;27(11):1508-13.
McKinney-Freeman et al., Muscle-derived hematopoietic stem cells are hematopoietic in origin. Proc Natl Acad Sci U S A. Feb. 5, 2002;99(3):1341-6.
McKinnon et al., Biophysically defined and cytocompatible covalently adaptable networks as viscoelastic 3D cell culture systems. Adv Mater. Feb. 12, 214;26(6):865-72.
McPherron et al., Regulation of skeletal muscle mass in mice by a new TGF-beta superfamily member. Nature. May 1, 1997;387(6628):83-90.
McWhorter et al., Modulation of macrophage phenotype by cell shape. Proc Natl Acad Sci U S A. Oct. 22, 2013;110(43):17253-8.
Meier et al., Peptide Nucleic Acids(PNAs)—Unusual Properties of Noionic Oligonucleotide Analogues. Angewandte Chemie, Int'l Edition. Aug. 1992;31(8):1008-1010.
Melero-Martin et al., Engineering robust and functional vascular networks in vivo with human adult and cord blood-derived progenitor cells. Circ Res. Jul. 18, 2008;103(2):194-202.
Melief et al., Immunotherapy of established (pre)malignant disease by synthetic long peptide vaccines. Nat Rev Cancer. May 2008;8(5):351-60.
Mellman et al., Dendritic cells: specialized and regulated antigen processing machines. Cell. Aug. 10, 2001;106(3):255-8.
Menetry et al., Suturing Versus Immobilization of a Muscle Laceration: A Morphological and Functional Study in a Mouse Model. Am J Sports Med. 1999;27(2):222-229.
Meraz et al., Mesoporous Silicon Particles for the Presentation of Tumor Antigens and Adjuvant for Anti-Cancer Immunity. Cancer Res. 2011;71(S24):159s-160s, Abstract #P1-01-12.
Merkel et al., Using mechanobiological mimicry of red blood cells to extend circulation times of hydrogel microparticles. Proc Natl Acad Sci U S A. Jan. 11, 2011;108(2):586-91.
Merriam-Webster, Transient. Merriam-Webster Dictionary. Web. Jul. 18, 2014. www.merriam-webster.com/dictionary/transient.
Metters et al., Fundamental studies of biodegradable hydrogels as cartilage replacement materials. Biomed Sci Instrum. 1999;35:33-8.
Meyer et al., Clinical investigations of Toll-like receptor agonists. Expert Opin Investig Drugs. Jul. 2008;17(7):1051-65.
Meylan et al., Intracellular pattern recognition receptors in the host response. Nature. Jul. 6, 2006;442(7098):39-44.
Mikos et al., Host response to tissue engineered devices. Adv Drug Deliv Rev. Aug. 3, 1998;33(1-2):111-139.
Miljkovic et al., Chondrogenesis, bone morphogenetic protein-4 and mesenchymal stem cells. Osteoarthritis Cartilage. Oct. 2008;16(10):1121-30.
Miller et al., Hepatocyte growth factor affects satellite cell activation and differentiation in regenerating skeletal muscle. Am J Physiol Cell Physiol. Jan. 2000;278(1):C174-81.

(56) References Cited

OTHER PUBLICATIONS

Miller et al., Lipopolysaccharide sequestrants: structural correlates of activity and toxicity in novel acylhomospermines. J Med Chem. Apr. 7, 2005;48(7):2589-99.
Miller et al., Melanoma. N Engl J Med. Jul. 6, 2006;355(1):51-65.
Miralles et al., Actin dynamics control SRF activity by regulation of its coactivator MAL. Cell. May 2, 2003;113(3):329-42.
Mitchell et al., The exogenous administration of basic fibroblast growth factor to regenerating skeletal muscle in mice does not enhance the process of regeneration. Growth Factors. 1996;13(1-2):37-55.
Miyata et al., Biomolecule-sensitive hydrogels. Adv Drug Deliv Rev. Jan. 17, 2002;54(1):79-98.
Mohan et al., Novel Porous, Polysaccharide Scaffolds for Tissue Engineering Applications. Trends Biomater Artif Organs. 2005;18(2):219-224.
Moioli et al., Matrices and scaffolds for drug delivery in dental, oral and craniofacial tissue engineering. Adv Drug Deliv Rev. May 30, 2007;59(4-5):308-24.
Molinari et al., Modification of surface membrane antigens by trypsin. Proc Soc Exp Biol Med. Apr. 1975;148(4):991-4.
Molloy et al., Movement and force produced by a single myosin head. Nature. Nov. 9, 1995;378(6553):209-12.
Mooney et al., Cytoskeletal filament assembly and the control of cell spreading and function by extracellular matrix. J Cell Sci. Jun. 1995;108 (Pt 6):2311-20.
Mooney et al., Switching from differentiation to growth in hepatocytes: control by extracellular matrix. J Cell Physiol. Jun. 1992;151(3):497-505.
Moser et al., Dendritic cell regulation of TH1-TH2 development. Nat Immunol. Sep. 2000;1(3):199-205.
Mulder et al., Wound Management: Past, Present, and Future. Clinicians' Pocket Guide to Chronic Wound Repair. Springhouse Corporation, Springhouse, Pennsylvania. 1998:85-90.
Muralidharan-Chari et al., ARF6-regulated shedding of tumor cell-derived plasma membrane microvesicles. Curr Biol. Dec. 1, 2009;19(22):1875-85.
Murdan, Electro-responsive drug delivery from hydrogels. J Control Release. Sep. 19, 2003;92(1-2):1-17.
Nagai et al., A variant of yellow fluorescent protein with fast and efficient maturation for cell-biological applications. Nat Biotechnol. Jan. 2002;20(1):87-90.
Naik et al., Development of plasmacytoid and conventional dendritic cell subtypes from single precursor cells derived in vitro and in vivo. Nat Immunol. Nov. 2007;8(11):1217-26.
Nair et al., Polymers as biomaterials for tissue engineering and controlled drug delivery. Adv Biochem Eng Biotechnol. 2006;102:47-90.
NCBI Accession No. 000749.2, Apr. 1, 2012.
NCBI Accession No. 000758, Apr. 1, 2012.
NCBI Accession No. 001020537, Jan. 30, 2011.
NCBI Accession No. 001020538, Jan. 30, 2011.
NCBI Accession No. 001020539, Jan. 30, 2011.
NCBI Accession No. 001020540, Jan. 30, 2011.
NCBI Accession No. 001028928, Jan. 30, 2011.
NCBI Accession No. 001193, May 3, 2014.
NCBI Accession No. 001552.2, Mar. 16, 2014.
NCBI Accession No. 001561.5, Mar. 16, 2014.
NCBI Accession No. 003237.2, May 25, 2014.
NCBI Accession No. 003265, Dec. 30, 2012.
NCBI Accession No. 003318.1, May 4, 2014.
NCBI Accession No. 003327.3, May 4, 2014.
NCBI Accession No. 003367, Jan. 30, 2011.
NCBI Accession No. 004119, Apr. 14, 2013.
NCBI Accession No. 004448.3, Apr. 23, 2014.
NCBI Accession No. 005009.2, Apr. 27, 2014.
NCBI Accession No. 005018.2, Apr. 27, 2014.
NCBI Accession No. 006274.2, Mar. 31, 2013.
NCBI Accession No. 017442, Apr. 14, 2012.
NCBI Accession No. 059138, Apr. 14, 2012.
NCBI Accession No. 181780.3, Jan. 27, 2014.
NCBI Accession No. 861445.3, Jan. 27, 2014.
Nehls et al., A novel, microcarrier-based in vitro assay for rapid and reliable quantification of three-dimensional cell migration and angiogenesis. Microvasc Res. Nov. 1995;50(3):311-22.
Nestle et al., Vaccination of melanoma patients with peptide- or tumorlysate-pulsed dendritic cells. Nature Medicine. Mar. 1, 1998;4(3):328-32.
Niamlang et al., Electrically controlled release of salicylic acid from poly(p-phenylene vinylene)/polyacrylamide hydrogels. Int J Pharm. Apr. 17, 2009;371(1-2):126-33.
Nichol et al., Cell-laden microengineered gelatin methacrylate hydrogels. Biomaterials. Jul. 2010;31(21):5536-44.
Nicodemus et al., Cell encapsulation in biodegradable hydrogels for tissue engineering applications. Tissue Eng Part B Rev. Jun. 2008;14(2):149-65.
Niessen et al., the alpha 6 beta 4 integrin is a receptor for both laminin and kalinin. Exp Cell Res. Apr. 1994;211(2):360-7.
Noguera-Troise et al., Blockade of Dll4 inhibits tumour growth by promoting non-productive angiogenesis. Nature. Dec. 21, 2006;444(7122):1032-7.
Ní Annaidh et al., Characterization of the anisotropic mechanical properties of excised human skin. J Mech Behav Biomed Mater. Jan. 2012;5(1):139-48.
O'Garra et al., Are dendritic cells afraid of commitment? Nat Immunol. Dec. 2004;5(12):1206-8.
O'Shea et al., Type 1 IFNs and regulation of TH1 responses: enigmas both resolved and emerge. Nat Immunol. Jul. 2000;1(1):17-9.
Ohashi et al., Surgical excision combined with autologous whole tumor cell vaccination is an effective therapy for murine neuroblastoma. J Pediatr Surg. Aug. 2006;41(8):1361-8.
Ohlstein et al., The stem cell niche: theme and variations. Curr Opin Cell Biol. Dec. 2004;16(6):693-9.
Oldenburg et al., TLR13 recognizes bacterial 23S rRNA devoid of erythromycin resistance-forming modification. Science. Aug. 31, 2012;337(6098):1111-5.
Oldenhove et al., Decrease of Foxp3+ Treg cell number and acquisition of effector cell phenotype during lethal infection. Immunity. Nov. 20, 2009;31(5):772-86.
Orner et al., Arrays for the combinatorial exploration of cell adhesion. J Am Chem Soc. Sep. 8, 2004;126(35):10808-9.
Osunkoya et al., Synthesis and fate of immunological surface receptors on cultured Burkitt lymphoma cells. Int J Cancer. Mar. 15, 1969;4(2):159-65.
Ota et al., Percutaneous subxiphoid access to the epicardium using a miniature crawling robotic device. Innovations (Phila). 2006 Fall;1(5):227-31.
Overwijk et al., Tumor regression and autoimmunity after reversal of a functionally tolerant state of self-reactive CD8+ T cells. J Exp Med. Aug. 18, 2003;198(4):569-80.
Ozawa et al., Microenvironmental VEGF concentration, not total dose, determines a threshold between normal and aberrant angiogenesis. J Clin Invest. Feb. 2004;113(4):516-27.
Padilla et al., Insufficient TLR activation contributes to the slow development of CD8+ T cell responses in Trypanosoma cruzi infection. J Immunol. Jul. 15, 2009;183(2):1245-52.
Page-McCaw et al., Matrix metalloproteinases and the regulation of tissue remodelling. Nat Rev Mol Cell Biol. Mar. 2007;8(3):221-33.
Pailler-Mattei et al., In vivo measurements of the elastic mechanical properties of human skin by indentation tests. Med Eng Phys. Jun. 2008;30(5):599-606.
Palacio et al., Interleukin 10 and tumor necrosis factor alpha gene expression in respiratory and peripheral muscles. Relation to sarcolemmal damage. Arch Bronconeumol. Jul. 2002;38(7):311-6.
Paradee et al., Effects of crosslinking ratio, model drugs, and electric field strength on electrically controlled release for alginate-based hydrogel. J Mater Sci Mater Med. Apr. 2012;23(4):999-1010.
Pardoll, The blockade of immune checkpoints in cancer immunotherapy. Nat Rev Cancer. Mar. 22, 2012;12(4):252-64.
Parekh et al., Modulus-driven differentiation of marrow stromal cells in 3D scaffolds that is independent of myosin-based cytoskeletal tension. Biomaterials. Mar. 2011;32(9):2256-64.

(56) References Cited

OTHER PUBLICATIONS

Parekkadan et al., Mesenchymal stem cell-derived molecules reverse fulminant hepatic failure. PLoS One. Sep. 26, 2007;2(9):e941.
Park et al., Photopolymerized hyaluronic acid-based hydrogels and interpenetrating networks. Biomaterials. Mar. 2003;24(6):893-900.
Parker et al., Effect of mitoxantrone on outcome of children with first relapse of acute lymphoblastic leukaemia (ALL R3): an open-label randomised trial. Lancet. Dec. 11, 2010;376(9757):2009-17.
Partridge et al., Conversion of mdx myofibres from dystrophin-negative to -positive by injection of normal myoblasts. Nature. Jan. 12, 1989;337(6203):176-9.
Pawlaczyk et al., Age-dependent biomechanical properties of the skin. Postepy Dermatol Alergol. Oct. 2013;30(5):302-6.
Pedersen et al., Induction of regulatory dendritic cells by dexamethasone and 1 alpha,25-Dihydroxyvitamin D(3). Immunol Lett. Jan. 30, 2004;91(1):63-9.
Pek et al., The effect of matrix stiffness on mesenchymal stem cell differentiation in a 3D thixotropic gel. Biomaterials. Jan. 2010;31(3):385-91.
Pelinkovic et al., Tissue engineering and gene therapy of the musculoskeletal system with muscle cells. Z Orthop Ihre Grenzgeb. Sep.-Oct. 2000;138(5):402-6.
Pena et al., Effects of TGF-beta and TGF-beta neutralizing antibodies on fibroblast-induced collagen gel contraction: implications for proliferative vitreoretinopathy. Invest Ophthalmol Vis Sci. May 1994;35(6):2804-8.
Peters et al., Engineering vascular networks in porous polymer matrices. J Biomed Mater Res. Jun. 15, 2002;60(4):668-78.
Peyton et al., the use of poly(ethylene glycol) hydrogels to investigate the impact of ECM chemistry and mechanics on smooth muscle cells. Biomaterials. Oct. 2006;27(28):4881-93.
Phillippi, Patterning of Multiple Cell Lineages from a Single Stem Cell Population. Annual Meeting of the American Society for Cell Biology. Dec. 10, 2006.
Pinho et al., PDGFRα and CD51 mark human nestin+ sphere-forming mesenchymal stem cells capable of hematopoietic progenitor cell expansion. J Exp Med. Jul. 1, 2013;210(7):1351-67.
Pluen et al., Role of tumor-host interactions in interstitial diffusion of macromolecules: cranial vs. subcutaneous tumors. Proc Natl Acad Sci U S A. Apr. 10, 2001;98(8):4628-33.
Pooyan et al., Conjugates bearing multiple formyl-methionyl peptides display enhanced binding to but not activation of phagocytic cells. Bioconjug Chem. Mar.-Apr. 2002;13(2):216-23.
Pope et al., Organ-specific regulation of the CD8 T cell response to Listeria monocytogenes infection. J Immunol. Mar. 1, 2001;166(5):3402-9.
Porter et al., Separation of Natural Populations of Coliform Bacteria from Freshwater and Sewage by Magnetic-Bead Cell Sorting. J Microbiol Meth. 1998;33(3):221-226.
Pouzet et al., Factors affecting functional outcome after autologous skeletal myoblast transplantation. Ann Thorac Surg. Mar. 2001;71(3):844-50; discussion 850-1.
Pulendran et al., Flt3-ligand and granulocyte colony-stimulating factor mobilize distinct human dendritic cell subsets in vivo. J Immunol. Jul. 1, 2000;165(1):566-72.
Qi et al., Patterned differentiation of individual embryoid bodies in spatially organized 3D hybrid microgels. Adv Mater. Dec. 7, 2010;22(46):5276-81.
Qin et al., Soft lithography for micro- and nanoscale patterning. Nat Protoc. Mar. 2010;5(3):491-502.
Qu et al., Development of approaches to improve cell survival in myoblast transfer therapy. J Cell Biol. Sep. 7, 1998;142(5):1257-67.
Qu-Petersen et al., Identification of a novel population of muscle stem cells in mice: potential for muscle regeneration. J Cell Biol. May 27, 2002;157(5):851-64.
Quezada et al., CTLA4 blockade and GM-CSF combination immunotherapy alters the intratumor balance of effector and regulatory T cells. J Clin Invest. Jul. 2006;116(7):1935-45.
Qui et al., Environment-sensitive hydrogels for drug delivery. Adv Drug Deliv Rev. Dec. 31, 2001;53(3):321-39.
Raeber et al., Molecularly engineered PEG hydrogels: a novel model system for proteolytically mediated cell migration. Biophys J. Aug. 2005;89(2):1374-88.
Rajagopalan et al., Regional angiogenesis with vascular endothelial growth factor in peripheral arterial disease: a phase II randomized, double-blind, controlled study of adenoviral delivery of vascular endothelial growth factor 121 in patients with disabling intermittent claudication. Circulation. Oct. 21, 2003;108(16):1933-8.
Ramón-Azcón et al., Gelatin methacrylate as a promising hydrogel for 3D microscale organization and proliferation of dielectrophoretically patterned cells. Lab Chip. Aug. 21, 2012;12(16):2959-69.
Randolph et al., Migration of dendritic cell subsets and their precursors. Annu Rev Immunol. 2008;26:293-316.
Ranganath et al., Harnessing the mesenchymal stem cell secretome for the treatment of cardiovascular disease. Cell Stem Cell. Mar. 2, 2012;10(3):244-58.
Raposo et al., Extracellular vesicles: exosomes, microvesicles, and friends. J Cell Biol. Feb. 18, 2013;200(4):373-83.
Rappolee et al., Macrophage-derived growth factors. Curr Top Microbiol Immunol. 1992;181:87-140.
Rapraeger, Syndecan-regulated receptor signaling. J Cell Biol. May 29, 2000;149(5):995-8.
Reddy et al., Exploiting lymphatic transport and complement activation in nanoparticle vaccines. Nat Biotechnol. Oct. 2007;25(10):1159-64.
Reimann et al., Satellite Cells in Normal and Regenerated Soleus Muscles of mdx and Control Mice. Eur J Neurosci. 1998;10:366, Abstract #153.07.
Reis E Sousa., Activation of dendritic cells: translating innate into adaptive immunity. Curr Opin Immunol. Feb. 2004;16(1):21-5.
Rhoads et al., Satellite cell-mediated angiogenesis in vitro coincides with a functional hypoxia-inducible factor pathway. Am J Physiol Cell Physiol. Jun. 2009;296(6):C1321-8.
Richards Grayson et al., Multi-pulse drug delivery from a resorbable polymeric microchip device. Nat Mater. Nov. 2003;2(11):767-72.
Richardson et al., Polymeric system for dual growth factor delivery. Nat Biotechnol. Nov. 2001;19(11):1029-34.
Riddle et al., Role of poly(lactide-co-glycolide) particle size on gas-foamed scaffolds. J Biomater Sci Polym Ed. 2004;15(12):1561-70.
Ridgway et al., Inhibition of Dll4 signalling inhibits tumour growth by deregulating angiogenesis. Nature. Dec. 21, 2006;444(7122):1083-7.
Rinderknecht et al., The amino acid sequence of human insulin-like growth factor I and its structural homology with proinsulin. J Biol Chem. Apr. 25, 1978;253(8):2769-76.
Rizzo et al., An improved cyan fluorescent protein variant useful for FRET. Nat Biotechnol. Apr. 2004;22(4):445-9.
Roccaro et al., BM mesenchymal stromal cell-derived exosomes facilitate multiple myeloma progression. J Clin Invest Apr. 2013;123(4):1542-55.
Rodriguez et al., Minimal "Self" peptides that inhibit phagocytic clearance and enhance delivery of nanoparticles. Science. Feb. 22, 2013;339(6122):971-5.
Rosenberg et al., Cancer immunotherapy: moving beyond current vaccines. Nat Med. Sep. 2004;10(9):909-15.
Roth et al., SC68896, a novel small molecule proteasome inhibitor, exerts antiglioma activity in vitro and in vivo. Clin Cancer Res. Nov. 1, 2009;15(21):6609-18.
Rowlands et al., Directing osteogenic and myogenic differentiation of MSCs: interplay of stiffness and adhesive ligand presentation. Am J Physiol Cell Physiol. Oct. 2008;295(4):C1037-44.
Rowley et al., Alginate hydrogels as synthetic extracellular matrix materials. Biomaterials. Jan. 1999;20(1):45-53.
Rowley et al., Alginate type and RGD density control myoblast phenotype. J Biomed Mater Res. May 2002;60(2):217-23.
Rowley et al., Biomaterials to Spatially Regulate Cell Fate. Adv Mater. Jun. 2002;14(12):886-889.
Rubin et al., Dissociation of heparan sulfate and receptor binding domains of hepatocyte growth factor reveals that heparan sulfate-c-met interaction facilitates signaling. J Biol Chem. Aug. 31, 2001;276(35):32977-83.

(56) References Cited

OTHER PUBLICATIONS

Ryten et al., ATP regulates the differentiation of mammalian skeletal muscle by activation of a P2X5 receptor on satellite cells. J Cell Biol. Jul. 22, 2002;158(2):345-55.
Ryu et al., The construction of three-dimensional micro-fluidic scaffolds of biodegradable polymers by solvent vapor based bonding of micro-molded layers. Biomaterials. Feb. 2007;28(6):1174-84.
Sacchetti et al., Self-renewing osteoprogenitors in bone marrow sinusoids can organize a hematopoietic microenvironment. Cell. Oct. 19, 2007;131(2):324-36.
Sakai et al., An injectable, in situ enzymatically gellable, gelatin derivative for drug delivery and tissue engineering. Biomaterials. Jul. 2009;30(20):3371-7.
Salem et al., Defining the antigen-specific T-cell response to vaccination and poly(I:C)/TLR3 signaling: evidence of enhanced primary and memory CD8 T-cell responses and antitumor immunity. J Immunother. May-Jun. 2005;28(3):220-8.
Salvador et al., Combination of immune stimulating adjuvants with poly(lactide-co-glycolide) microspheres enhances the immune response of vaccines. Vaccine. Jan. 11, 2012;30(3):589-96.
Salvay et al., Inductive tissue engineering with protein and DNA-releasing scaffolds. Mol Biosyst. Jan. 2006;2(1):36-48.
Sano et al., Swift development of protective effector functions in naive CD8(+) T cells against malaria liver stages. J Exp Med. Jul. 16, 2001;194(2):173-80.
Sansonetti, The innate signaling of dangers and the dangers of innate signaling. Nat Immunol. Dec. 2006;7(12):1237-42.
Sarkar et al., Condensation of oligonucleotides assembled into nicked and gapped duplexes: potential structures for oligonucleotide delivery. Nucleic Acids Res. Jan. 7, 2005;33(1):143-51.
Sato, Human dendritic cells. Biotherapy. Nov. 2004;18(6):467-77.
Saxena et al., Skeletal muscle tissue engineering using isolated myoblasts on synthetic biodegradable polymers: preliminary studies. Tissue Eng. Dec. 1999;5(6):525-32.
Schaefer et al., Innate immunity in the human female reproductive tract: antiviral response of uterine epithelial cells to the TLR3 agonist poly(I:C). J Immunol. Jan. 15, 2005;174(2):992-1002.
Scheel et al., Toll-like receptor-dependent activation of several human blood cell types by protamine-condensed mRNA. Eur J Immunol. May 2005;35(5):1557-66.
Schijns et al., Mice lacking IL-12 develop polarized Th1 cells during viral infection. J Immunol. Apr. 15, 1998;160(8):3958-64.
Schnorrer et al., The dominant role of CD8+ dendritic cells in cross-presentation is not dictated by antigen capture. Proc Natl Acad Sci U S A. Jul. 11, 2006;103(28):10729-34.
Schofield, The relationship between the spleen colony-forming cell and the haemopoietic stem cell. Blood Cells. 1978;4(1-2):7-25.
Schuler et al., The use of dendritic cells in cancer immunotherapy. Curr Opin Immunol. Apr. 2003;15(2):138-47.
Schwartz, Integrins and extracellular matrix in mechanotransduction. Cold Spring Harb Perspect Biol. Dec. 2010;2(12):a005066.
Seale et al., Pax7 is required for the specification of myogenic satellite cells. Cell. Sep. 15, 2000;102(6):777-86.
Sensi et al., Unique tumor antigens: evidence for immune control of genome integrity and immunogenic targets for T cell-mediated patient-specific immunotherapy. Clin Cancer Res. Sep. 1, 2006;12(17):5023-32.
Shakweh et al., Design and characterisation of poly(lactide-co-glycolide) small particulate systems for the delivery of immunostimulant CpG oligonucleotide. J Nanosci Nanotechnol. Sep.-Oct. 2006;6(9-10):2811-20.
Shaner et al., Improved monomeric red, orange and yellow fluorescent proteins derived from *Discosoma* sp. red fluorescent protein. Nat Biotechnol. Dec. 2004;22(12):1567-72.
Shansky et al., A simplified method for tissue engineering skeletal muscle organoids in vitro. In Vitro Cell Dev Biol Anim. Oct. 1997;33(9):659-61.
Sheehan et al., Skeletal muscle satellite cell proliferation in response to members of the fibroblast growth factor family and hepatocyte growth factor. J Cell Physiol. Dec. 1999;181(3):499-506.

Sheridan et al., Bioabsorbable polymer scaffolds for tissue engineering capable of sustained growth factor delivery. J Control Release. Feb. 14, 2000;64(1-3):91-102.
Shi et al., A novel Toll-like receptor that recognizes vesicular stomatitis virus. J Biol Chem. Feb. 11, 2011;286(6):4517-24.
Shi et al., Granulocyte-macrophage colony-stimulating factor (GM-CSF) and T-cell responses: what we do and don't know. Cell Res. Feb. 2006;16(2):126-33.
Shin et al., Contractile forces sustain and polarize hematopoiesis from stem and progenitor cells. Cell Stem Cell. Jan. 2, 2014;14(1):81-93.
Shin et al., Lamins regulate cell trafficking and lineage maturation of adult human hematopoietic cells. Proc Natl Acad Sci U S A. Nov. 19, 2013;110(47):18892-7.
Shin et al., Myosin-II inhibition and soft 2D matrix maximize multinucleation and cellular projections typical of platelet-producing megakaryocytes. Proc Natl Acad Sci U S A. Jul. 12, 2011;108(28):11458-63.
Shoichet et al., Stability of hydrogels used in cell encapsulation: An in vitro comparison of alginate and agarose. Biotechnol Bioeng. May 20, 1996;50(4):374-81.
Shortman et al., Steady-state and inflammatory dendritic-cell development. Nat Rev Immunol. Jan. 2007;7(1):19-30.
Sick et al., WNT and DKK determine hair follicle spacing through a reaction-diffusion mechanism. Science. Dec. 1, 2006;314(5804):1447-50.
Siegwart et al., Synthesis, characterization, and in vitro cell culture viability of degradable poly(N-isopropylacrylamide-co-5,6-benzo-2-methylene-1,3-dioxepane)-based polymers and crosslinked gels. J Biomed Mater Res A. Nov. 2008;87(2):345-58.
Silva et al., Effects of VEGF temporal and spatial presentation on angiogenesis. Biomaterials. Feb. 2010;31(6):1235-41.
Silva et al., Material-based deployment enhances efficacy of endothelial progenitor cells. Proc Natl Acad Sci U S A. Sep. 23, 2008;105(38):14347-52.
Silva et al., Spatiotemporal control of vascular endothelial growth factor delivery from injectable hydrogels enhances angiogenesis. J Thromb Haemost. Mar. 2007;5(3):590-8.
Singer et al., Cutaneous wound healing. N Engl J Med. Sep. 2, 1999;341(10):738-46.
Skokos et al., CD8- DCs induce IL-12-independent Th1 differentiation through Delta 4 Notch-like ligand in response to bacterial LPS. J Exp Med. Jul. 9, 2007;204(7):1525-31.
Skuk et al., Efficacy of myoblast transplantation in nonhuman primates following simple intramuscular cell injections: toward defining strategies applicable to humans. Exp Neurol. May 2002;175(1):112-26.
Skuk et al., Myoblast transplantation: the current status of a potential therapeutic tool for myopathies. J Muscle Res Cell Motil. 2003;24(4-6):285-300.
Smidsrød et al., Alginate as immobilization matrix for cells. Trends Biotechnol. Mar. 1990;8(3):71-8.
Sohier et al., Critical factors in the design of growth factor releasing scaffolds for cartilage tissue engineering. Expert Opin Drug Deliv. May 2008;5(5):543-66.
Solon et al., Fibroblast adaptation and stiffness matching to soft elastic substrates. Biophys J. Dec. 15, 2007;93(12):4453-61.
Stachowiak et al., Inverse opal hydrogel-collagen composite scaffolds as a supportive microenvironment for immune cell migration. J Biomed Mater Res A. Jun. 1, 2008;85(3):81528.
Steinman et al., Taking dendritic cells into medicine. Nature. Sep. 27, 2007;449(7161):419-26.
Storrie et al., Sustained delivery of plasmid DNA from polymeric scaffolds for tissue engineering. Adv Drug Deliv Rev. Jul. 7, 2006;58(4):500-14.
Straub et al., Animal models for muscular dystrophy show different patterns of sarcolemmal disruption. J Cell Biol. Oct. 20, 1997;139(2):375-85.
Sun et al., Biomimetic interpenetrating polymer network hydrogels based on methacrylated alginate and collagen for 3D pre-osteoblast spreading and osteogenic differentiation. Soft Matter. Jan. 12, 2012;8:2398-2404.

(56) References Cited

OTHER PUBLICATIONS

Sun et al., Highly stretchable and tough hydrogels. Nature. Sep. 6, 2012;489(7414):133-6.
Sun et al., Sustained vascular endothelial growth factor delivery enhances angiogenesis and perfusion in ischemic hind limb. Pharm Res. Jul. 2005;22(7):1110-6.
Suri et al., Photopatterned collagen-hyaluronic acid interpenetrating polymer network hydrogels. Acta Biomater. Sep. 2009;5(7):2385-97.
Swift et al., Nuclear lamin-A scales with tissue stiffness and enhances matrix-directed differentiation. Science. Aug. 30, 2013;341(6149):1240104.
Syed et al., Stem cell therapy market. Nat Rev Drug Discov. Mar. 2013;12(3):185-6.
Tabata et al., Enhanced Vascularization and Tissue Granulation by Basic Fibroblast Growth Factor Impregnated in Gelatin Hydrogels. Journal of Controlled Release. Sep. 1994;31(2):189-199.
Takahashi et al., Induction of pluripotent stem cells from adult human fibroblasts by defined factors. Cell. Nov. 30, 2007;131(5):861-72.
Takeshita et al., Therapeutic angiogenesis. A single intraarterial bolus of vascular endothelial growth factor augments revascularization in a rabbit ischemic hind limb model. J Clin Invest. Feb. 1994;93(2):662-70.
Tamura et al., Immunotherapy of tumors with autologous tumor-derived heat shock protein preparations. Science. Oct. 3, 1997;278(5335):117-20.
Tanaka et al., Collapse of gels in an electric field. Science. Oct. 29, 1982;218(4571):467-9.
Tannous, Gaussia luciferase reporter assay for monitoring biological processes in culture and in vivo. Nat Protoc. 2009;4(4):582-91.
Tatsumi et al., GF/SF is present in normal adult skeletal muscle and is capable of activating satellite cells. Dev Biol. Feb. 1, 1998;194(1):114-28.
Ten Dijke et al., Growth Factors for Wound Healing. Nat Biotechnol. 1989;7:793-798.
Thomas et al., Intravenous infusion of bone marrow in patients receiving radiation and chemotherapy. N Engl J Med. Sep. 12, 1957;257(11):491-6.
Thurner et al., Vaccination with mage-3A1 peptide-pulsed mature, monocyte-derived dendritic cells expands specific cytotoxic T cells and induces regression of some metastases in advanced stage IV melanoma. J Exp Med. Dec. 6, 1999;190(11):1669-78.
Thurston et al., The Delta paradox: DLL4 blockade leads to more tumour vessels but less tumour growth. Nat Rev Cancer. May 2007;7(5):327-31.
Tidball, Inflammatory cell response to acute muscle injury. Med Sci Sports Exerc. Jul. 1995;27(7):1022-32.
Tomer et al., Electrically Controlled Release of Macromolecules from Cross-Linked Hyaluronic Acid Hydrogels. Journal of Controlled Release. Mar. 1995:33(3):405-413.
Tong et al., Engineering interpenetrating network hydrogels as biomimetic cell niche with independently tunable biochemical and mechanical properties. Biomaterials. Feb. 2014;35(6):1807-15.
Tourniaire et al., Polymer microarrays for cellular adhesion. Chem Commun (Camb). May 28, 2006;(20):2118-20.
Trappmann et al., Extracellular-matrix tethering regulates stem-cell fate. Nat Mater. May 27, 2012;11(7):642-9.
Trappmann et al., How cells sense extracellular matrix stiffness: a material's perspective. Curr Opin Biotechnol. Oct. 2013;24(5):948-53.
Tsien, The green fluorescent protein. Annu Rev Biochem. 1998;67:509-44.
Turing, Discussion: Turing's Theory of Morphogenesis—Its Influence on Modelling Biological Pattern and Form. Bull Math Biol. 1990;52(1-2):119-159.
Turing, The Chemical Basis of Morphogenesis. Philosophical Transactions of the Royal Society of London. Series B. 1952;237(641):37-72.

Uchida et al., Immunization by particle bombardment of antigen-loaded poly-(DL-lactide-co-glycolide) microspheres in mice. Vaccine. Mar. 15, 2006;24(12):2120-30.
Ugarte et al., Notch signaling enhances osteogenic differentiation while inhibiting adipogenesis in primary human bone marrow stromal cells. Exp Hematol. Jul. 2009;37(7):867-875.
Uhlenbruck, Action of proteolytic enzymes on the human erythrocyte surface. Nature. Apr. 8, 1961;190:181.
Ulrich et al., Probing cellular mechanobiology in three-dimensional culture with collagen-agarose matrices. Biomaterials. Mar. 2010;31(7):1875-84.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Urbanek et al., Stem cell niches in the adult mouse heart. Proc Natl Acad Sci U S A. Jun. 13, 2006;103(24):9226-31.
Van Der Bruggen et al., Peptide database: T cell-defined tumor antigens. Cancer Immun. Available at: http://www.cancerimmunity.org/peptide/ (2013).
Van Duin et al., Triggering TLR signaling in vaccination. Trends Immunol. Jan. 2006;27(1):49-55.
Vandenburgh et al., Tissue-engineered skeletal muscle organoids for reversible gene therapy. Hum Gene Ther. Nov. 10, 1996;7(17):2195-200.
Venturoni et al., Investigations into the polymorphism of rat tail tendon fibrils using atomic force microscopy. Biochem Biophys Res Commun. Apr. 4, 2003;303(2):508-13.
Vieira et al., The bulk of endogenously produced IgG2a is eliminated from the serum of adult C57BL/6 mice with a half-life of 6-8 days. Eur J Immunol. Jul. 1986;16(7):871-4.
Vieira et al., The half-lives of serum immunoglobulins in adult mice. Eur J Immunol. Feb. 1988;18(2):313-6.
Villadangos et al., Intrinsic and cooperative antigen-presenting functions of dendritic-cell subsets in vivo. Nat Rev Immunol. Jul. 2007;7(7):543-55.
Villadangos, Presentation of antigens by MHC class II molecules: getting the most out of them. Mol Immunol. Sep. 2001;38(5):329-46.
Vincent et al., Stem cell differentiation: Post-degradation forces kick in. Nat Mater. May 2013;12(5):384-6.
Vogel et al., Local force and geometry sensing regulate cell functions. Nat Rev Mol Cell Biol. Apr. 2006;7(4):265-75.
Von Dassow et al., The segment polarity network is a robust developmental module. Nature. Jul. 13, 2000;406(6792):188-92.
W.H.O., World Health Organization, Global Burden of Musculoskeletal Disease Revealed in new WHO Report. Bull World Health Organ. 2003;81(11):853-854.
W.H.O., World Health Organization, The World Health Report 2004: Changing History. The World Health Report. 2004:1-169.
Wakim et al., Dendritic cell-induced memory T cell activation in nonlymphoid tissues. Science. Jan. 11, 2008;319(5860):198-202.
Waldron-Lynch et al., Advances in Type 1 diabetes therapeutics: immunomodulation and beta-cell salvage. Endocrinol Metab Clin North Am. Jun. 2009;38(2):303-17.

(56) References Cited

OTHER PUBLICATIONS

Wan et al., Peritoneal macrophage uptake, pharmacokinetics and biodistribution of macrophage-targeted PEG-fMLF (N-formyl-methionyl-leucyl-phenylalanine) nanocarriers for improving HIV drug delivery. Pharm Res. Nov. 2007;24(11):2110-9.
Wang et al., Biological activity of bevacizumab, a humanized anti-VEGF antibody in vitro. Angiogenesis. 2004;7(4):335-45.
Wang et al., Evolution of new nonantibody proteins via iterative somatic hypermutation. Proc Natl Acad Sci U S A. Nov. 30, 2004;101(48):16745-9.
Wang et al., Mechanotransduction at a distance: mechanically coupling the extracellular matrix with the nucleus. Nat Rev Mol Cell Biol. Jan. 2009;10(1):75-82.
Wang et al., Photothermal effects of supramolecularly assembled gold nanoparticles for the targeted treatment of cancer cells. Angew Chem Int Ed Engl. May 17, 2010;49(22):3777-81.
Wang-Gillam et al., A phase I study of IMP321 and gemcitabine as the front-line therapy in patients with advanced pancreatic adenocarcinoma. Invest New Drugs. Jun. 2013;31(3):707-13.
Warner et al., Cyclooxygenases: new forms, new inhibitors, and lessons from the clinic. FASEB J. May 2004;18(7):790-804.
Wei et al., Global mapping of H3K4me3 and H3K27me3 reveals specificity and plasticity in lineage fate determination of differentiati ng CD4+ T cells. Immunity. Jan. 16, 2009;30(1):155-67.
Weisenberger et al., Comprehensive DNA Methylation Analysis on the Illumina® Infinium® Assay Platform. Illumina, Inc., 4 pages, Mar. 25, 2008.
Weiss et al., The demonstration of rupture of cell surfaces by an immunological technique. Exp Cell Res. Apr. 1963;30:331-8.
Wen et al., Mechanically Robust Gelatin-Alginate IPN Hydrogels by a Combination of Enzymatic and Ionic Crosslinking Approaches. Macromol Mater Eng. Apr. 2014;299(4):504-513.
Wernig et al., Function of skeletal muscle tissue formed after myoblast transplantation into irradiated mouse muscles. J Physiol. Jan. 15, 2000;522 Pt 2:333-45.
White et al., Leukemia inhibitory factor enhances regeneration in skeletal muscles after myoblast transplantation. Muscle Nerve. May 2001;24(5):695-7.
Wieland et al., Engineering molecular circuits using synthetic biology in mammalian cells. Annu Rev Chem Biomol Eng. 2012;3:209-34.
Wipff et al., Myofibroblast contraction activates latent TGF-beta1 from the extracellular matrix. J Cell Biol. Dec. 17, 2007;179(6):1311-23.
Wong et al., Focal adhesion kinase links mechanical force to skin fibrosis via inflammatory signaling. Nat Med. Dec. 11, 2011;18(1):148-52.
Wong et al., Mechanical force prolongs acute inflammation via T-cell-dependent pathways during scar formation. FASEB J. Dec. 2011;25(12):4498-510.
Wong et al., Pushing back: wound mechanotransduction in repair and regeneration. J Invest Dermatol. Nov. 2011;131(11):2186-96.
Wozniak et al., Mechanotransduction in development: a growing role for contractility. Nat Rev Mol Cell Biol. Jan. 2009;10(1):34-43.
Wright et al., Muscle-based gene therapy and tissue engineering for the musculoskeletal system. Drug Discov Today. Jul. 1, 2001;6(14):728-733.

Xie et al., Preparation and Application of Surface-Coated Superparamagnetic Nanobeads in the Isolation of Genomic DNA. J Magn Magnetic Mater. Jun. 2004;277(1-2):16-23.
Yamazaki et al., CD8+ CD205+ splenic dendritic cells are specialized to induce Foxp3+ regulatory T cells. J Immunol. Nov. 15, 2008;181(10):6923-33.
Yancopoulos et al., Vascular-specific growth factors and blood vessel formation. Nature. Sep. 14, 2000;407(6801):242-8.
Yang, Fan et al., The effect of incorporating RGD adhesive peptide in polyethylene glycol diacrylate hydrogel on osteogenesis of bone marrow stromal cells. Biomaterials. Oct. 2005;26(30):5991-8.
Yeung et al., Effects of substrate stiffness on cell morphology, cytoskeletal structure, and adhesion. Cell Motil Cytoskeleton. Jan. 2005;60(1):24-34.
Yoo et al., Bio-inspired, bioengineered and biomimetic drug delivery carriers. Nat Rev Drug Discov. Jul. 1, 2011;10(7):521-35.
Yoon, Hidden Markov Models and their Applications in Biological Sequence Analysis. Curr Genomics. Sep. 2009;10(6):402-15.
Young et al., Gelatin as a delivery vehicle for the controlled release of bioactive molecules. J Control Release. Dec. 5, 2005;109(1-3):256-74.
Yu et al., Induced pluripotent stem cell lines derived from human somatic cells. Science. Dec. 21, 2007;318(5858):1917-20.
Yuen et al., Mimicking nature by codelivery of stimulant and inhibitor to create temporally stable and spatially restricted angiogenic zones. Proc Natl Acad Sci U S A. Oct. 19, 2010;107(42):17933-8.
Yuk et al., Electric current-sensitive drug delivery systems using sodium alginate/polyacrylic acid composites. Pharm Res. Jul. 1992;9(7):955-7.
Zammit et al., Kinetics of myoblast proliferation show that resident satellite cells are competent to fully regenerate skeletal muscle fibers. Exp Cell Res. Nov. 15, 2002;281(1):39-49.
Zammit et al., Muscle satellite cells adopt divergent fates: a mechanism for self-renewal? J Cell Biol. Aug. 2, 2004;166(3):347-57.
Zeltinger et al., Effect of pore size and void fraction on cellular adhesion, proliferation, and matrix deposition. Tissue Eng. Oct. 2001;7(5):557-72.
Zemel et al., Optimal matrix rigidity for stress fiber polarization in stem cells. Nat Phys. Jun. 1, 2010;6(6):468-473.
Zhang et al., A comparative study of the antigen-specific immune response induced by co-delivery of CpG ODN and antigen using fusion molecules or biodegradable microparticles. J Pharm Sci. Dec. 2007;96(12):3283-92.
Zhang et al., A tension-induced mechanotransduction pathway promotes epithelial morphogenesis. Nature. Mar. 3, 2011;471(7336):99-103.
Zhang et al., Talin depletion reveals independence of initial cell spreading from integrin activation and traction. Nat Cell Biol. Sep. 2008;10(9):1062-8.
Zhao et al., Active scaffolds for on-demand drug and cell delivery. Proc Natl Acad Sci U S A. Jan. 4, 2011;108(1):67-72.
Zhao et al., Directed cell migration via chemoattractants released from degradable microspheres. Biomaterials. Aug. 2005;26(24):5048-63.
Zhao et al., Stress-relaxation behavior in gels with ionic and covalent crosslinks. J Appl Phys. Mar. 15, 2010;107(6):63509.
Zhou et al., Microstructure and Mechanical Properties of Poly(L-lactide) Scaffolds Fabricated by Gelatin Particle Leaching Method. J Appl Polymer Sci. Nov. 5, 2005:1373-1379.

* cited by examiner

SCAFFOLDS FOR CELL COLLECTION OR ELIMINATION

RELATED APPLICATIONS

This application is a continuation of U.S. patent application Ser. No. 12/665,761, filed on Dec. 21, 2009, which is a 35 U.S.C. § 371 national stage filing of International Application No. PCT/US2008/007258, filed on Jun. 11, 2008, which in turn claims the benefit of U.S. Provisional Patent Application No. 60/936,743, filed Jun. 21, 2007. The entire contents of the foregoing applications are hereby incorporated by reference.

SEQUENCE LISTING

The instant application contains a Sequence Listing which has been submitted electronically in ASCII format and is hereby incorporated by reference in its entirety, Said ASCII copy, created Sep. 5, 2017, is named 117823-12403_ST25.txt and is 4.0 kilobytes in size.

FIELD OF THE INVENTION

The present invention relates to the field of systemic disease prevention, management, and elimination.

BACKGROUND OF THE INVENTION

Some of the most prevalent and debilitating diseases in the US, and throughout the world, have several fundamental characteristics in common. First, they can be caused by subpopulations of cells which, through a variety of mechanisms, begin to impair the ability of their host to thrive. Second, the degree of severity of disease is closely linked with the ability of these undesirable cell populations to disseminate throughout multiple physiological systems. The difficulty that medicine faces in treating any condition is selectivity. The ultimate goal of treating disease is to discover a method of eliminating only the subpopulations of cells that impair function, while simultaneously sparing healthy, uninvolved, cell populations in close proximity. Many conventional drug and surgical remedies inflict damaging side effects which can either induce a new condition because they are imprecise, and thus inadvertently damage healthy cells, or further challenge the ability of an individual to thrive by making them more vulnerable to future disease.

SUMMARY OF THE INVENTION

The present invention addresses a solution to multiple obstacles associated with the in vivo elimination of distinct cell populations. First and foremost, unlike drug remedies, the device is capable of capturing, and therefore sequestering, undesirable cells either within an internal compartment or along its external surface by either filtering cells through pores in the external surface or binding cells to adhesive proteins along either its internal or external surfaces. This is a critically important innovation, because the mechanisms employed by the device to eliminate those cells which it contacts are engineered to be highly selective for only targeted cells, allowing surrounding tissue to remain unaffected. Moreover, this selectivity is particularly impressive when the device is administered systemically, in which case it is capable of first identifying, then capturing, and, if desired, eliminating cells that are in the process of spreading disease while preserving epithelial linings and other non-target tissues, as well as sparing passing blood and immune cells from interaction with treatments. Furthermore, when the target of the device is a robust cell type that requires a highly toxic agent to induce cell death, the ability of this devise to sequester cells away from their host microenvironments is particularly advantageous because concentrating these cells in a compartment without access to signaling proteins, nutrients, or adequate levels of oxygen itself induces cell death, eliminating the need to introduce a toxic substance into the host. Finally, the device overcomes obstacles such as antibiotic resistance and drug tolerance by using sequestration, which does not introduce compounds systemically, as well as a bioactive composition that includes molecules or cells capable of activating signaling pathways within the target cell population that will lead to self-destruction.

This device includes a scaffold composition which incorporates or is coated with a bioactive composition; the device attracts, adheres, captures and eliminates targeted undesirable cells. The device executes these functions by a variety of methods that include or exclude the use of a bioactive composition. Depending on the application for which the device is used, the device regulates capture and survival through the physical or chemical characteristics of the scaffold itself. For example, the scaffold composition is differentially permeable, allowing cell passage only in certain physical areas of the scaffold. The permeability of the scaffold composition is regulated, for example, by selecting or engineering a material for greater or smaller pore size, density, polymer cross-linking, stiffness, toughness, ductility, or viscoelascticity. The scaffold composition contains physical channels or paths through which cells contact a specific bioactive composition within the device or move into an intended compartment within the device. The scaffold composition is optionally organized into compartments or layers, each with a different permeability, so that cells are sorted or filtered in order to exclude targeted subpopulations from accessing or participating in the host environment while simultaneously allowing non-targeted cell types to pass through the device unaltered. Migration of target cell populations through the device is also regulated by the degradation, de- or re-hydration, oxygenation, chemical or pH alteration, or ongoing self-assembly of the scaffold composition. These processes are driven by diffusion or cell-secretion of enzymes or other reactive chemicals. Following their capture, resident cells are prohibited from accessing the host environment, which provides necessary means for survival including host cell contact, signaling molecules, sustaining nutrients, and adequate levels of oxygen. Thus, having been removed from the context of any biological niche, captured cells are sequestered or eliminated. Once the captured population is removed the scaffold composition either degrades or is collected from the subject.

Exemplary cell types that are targeted for sequestration or quarantine by this device, and are eliminated by environmental deprivation alone, and without the aid of a bioactive composition, include circulating microorganisms such as bacteria, viruses, parasites, worms, protozoa, as well as mobile mammalian tissues including immune cells, metastatic cancer cells, sickle-shaped or damaged blood cells, and epithelial cells that have lost intercellular contacts.

Optionally, a bioactive composition with means to physically bind and adhere target cells to the scaffold composition is added to ensure that cells do not escape from the scaffold once they have contacted it. Exemplary components of such an adhesive bioactive composition are either found in nature or engineered, and are listed below alongside the cell types for which they are specific.

Alternatively or in addition, the processes of cell attraction, adhesion, capture, or elimination are regulated primarily by one or more bioactive compositions. By varying the concentration of attractive molecules, the bioactive composition draws mobile or circulating cells into the device. The following are examples of attractive compounds that are used alone or in combinations to attract mobile cells to the scaffold composition: multivalent acrylamide polymers or polylysine tagged with either a sugar (galactose, fucose, ribose, or any derivatives thereof) or an amino acid (aspartate, leucine, serine) to attract bacteria; cytokines or chemokines to attract immune and metastatic cancer cells. By including particular subsets of adhesion molecules, the bioactive composition serves a selectivity function, second to the sorting and filtering function performed by the scaffold composition itself, wherein adhesion molecules that preferentially bind target cell types are incorporated into the device to differentiate between morphologically or physically similar target and non-target cell populations that might otherwise pass through porous filters. For example, the adhesion molecules including, but not limited to, the following are incorporated into bioactive compositions with means to capture microorganisms: adhesins to bind prokaryotes; polysaccharides to bind bacteria; sugar sialic acid, capsid-binding proteins, viral attachment proteins, isolated plasma membrane fractions from cellular targets to bind viruses. Alternatively adhesion molecules including, but not limited to, the following are incorporated into bioactive compositions to capture eukaryotic, or mammalian, cells: integrins, Ig superfamily members, cadherins, or selectins.

Unique combinations of attraction or adhesion molecules incorporated into the scaffold composition to differentially capture target cell populations, wherein target cell capture is either permanent or temporary depending upon which duration is most advantageous for the intended use of the device. For example, adhesive interactions with microorganisms can either be permanent or temporary depending upon the function of the device. If the device is used as a diagnostic tool for which it will be collected, semi-permanent, strong but temporary, adhesive interactions are preferred because the microorganisms can not escape from the device in the host, but can be separated from the device upon collection to allow for the isolation and identification of the captured cells by a laboratory technician. However, if the device is used as a treatment for a known infection, a permanent adhesive interaction is preferred because the microorganisms are sequestered and killed while attached to the scaffold composition and do not need to be recovered. Alternatively, the scaffold itself can be dissolved in vitro following collection to release microorganisms or mammalian cells adhered to the bioactive composition for further analysis.

By varying the components of the bioactive composition that lead to cell death, the device eliminates cells efficiently with minimal disturbance to non-targeted cell types. The device employs two primary mechanisms. By the first mechanism, target cell populations are attracted to or selectively filtered through the scaffold composition where they bind adhesive agents incorporated into the scaffold. These captured cells are then eliminated by a variety of mechanisms, all of which act exclusively within the device. By the second mechanism, the device is placed in a specific location where a target cell population resides, where it contacts neighboring cells and is anchored, e.g., adheres, in order to prevent diffusion or migration of the device. In this scenario, the closely juxtaposed cells are exposed to particles, compounds, or engineered cells that are released or allowed to diffuse from the device, disseminating only a short distance. Target cell specificity, in this second case, is achieved by the differential placement of the device, the specific compounds released, or manipulation of cell types housed within the device allowing them only to attack cells having a characteristic morphology or surface protein expression profile.

The following descriptions elucidate specific means by which target cell populations are eliminated either following capture and sequestration into the scaffold composition, or following release of particles, compounds, drug agents, or engineered cell types into the tissue surrounding an implanted device.

Antibiotic compounds including, but not limited to, amikacin, gentamicin, kanamycin, neomycin, netilmicin, streptomycin, tobramycin, teicoplanin, vancomycin, azithromycin, clarithromycin, clarithromycin, dirithromycin, erythromycin, roxithromycin, troleandomycin, amoxicillin, ampicillin, azlocillin, carbenicillin, clozacillin, dicloxacillin, flucozacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, or tetracycline are incorporated, alone or in any combination thereof, into a bioactive composition within devices used for treatment of bacterial infection.

Antiviral compounds including, but not limited to, amantadine, rimantadine, pleconaril, acyclovir, zidovudine, lamivudine, fomivirsen, zanamivir, oseltamivir, or interferon alpha are incorporated, alone or in any combination thereof, into a bioactive composition within devices used for treatment of viral infection.

Antiparasitic compounds including, but not limited to, ivermectin, diethylcarbamazine, eflornithine, melarsoprol, pentamidine, suramin, pentavalent antimonials, liposomal amphotericin B, miltefosine, chloroquine, sulphadoxine, mefloquine, artemisinins, artemether, lumefatrine, atovaquone, proguanil, chlorproguanil, dapsone, fosmidomycin, DB289, pyrimethamine, cycloguanil, sulphamethoxazole, difluoromethylornithine, antifungal trizoles (for example, posaconazole), risedronate, levamisole, or albendazole, are incorporated, alone or in any combination thereof, into a bioactive composition within devices used for treatment of parasitic, protozoan, or worm-derived infections.

Antifungal compounds including, but not limited to, sertaconazole, sulconazole, tioconazole, fluconazole, itraconazole, isavuconazole, ravuconazole, posaconizole, voriconazole, terconizole, terbinafine, amorolfine, naftifine, butenafine, anidulafungin, caspofungin, micofungin, ciclopirox, flucytosine, griseofulvin, haloprogin, tolnaftate, undecylenic acid, or ampho B lipid, are incorporated, alone or in any combination thereof, into a bioactive composition within devices used for treatment of fungal infections.

Mammalian cell types are targeted and eliminated by the device. To eliminate captured cells the device utilizes a variety of mechanisms. Bioactive compositions incorporated into the scaffold composition with means to destroy captured cells include, but are not limited to, phagocytic cells with or without compounds having means to augment their activity; engineered viruses; humanized monoclonal antibodies to activate the immune system, bind and block receptor activity, or specifically deliver a toxin with which it is bound; pro-apoptotic ligands, such as FasL, TNF, TRAIL, and caspase-activators; radioactive isotopes, such as Bismuth-213 Holmium-66, Iodine-125, Iodine-131, and Lutetium-177; toxins, including hemotoxins, necrotoxins, and neurotoxins; and chemotherapy agents.

To accomplish long-lasting weight-loss for individuals who are unable to control their fat intake or storage by any other method, and to avoid risks associated with surgical interventions, one or more device(s) are implanted on or around adipose tissue, usually located either beneath the skin (subcutaneous) or around internal organs (intraperitoneal cavity), wherein one or more bioactive compositions conjugated to the scaffold composition adhere adipocytes or pre-adipocytes (precursors that give rise to adipocytes) and induce cell death following contact with either the scaffold composition or a diffusible bioactive composition released from the device. The abundance and placement of implanted devices controls the degree to which adipocytes and pre-adipocytes are targeted, although ultimately, some tissue remains, as these cells are only undesirable when overly expanded or abundant, particularly when they reside in close proximity to and inhibit the function of vital internal organs. White adipose tissue (WAT) is targeted by the device because the alternate type, brown adipose tissue, performs functions essential for the health of the subject. Exemplary surface proteins that are used by the bioactive composition to specifically recognize immature and mature white adipocytes include, but are not limited to, serum amyloid A (SAA), adipophilin, and/or lipoprotein lipase (LPL). Adipocytes or their precursors, are eliminated by induction of apoptosis via a bioactive composition released from a stationary, and therefore implanted, device.

Neoplastic cell types, malignant or benign, are targeted and eliminated by the device. Cells that contribute to the formation of malignant neoplasms are targeted as a treatment for cancer while those cells that contribute to benign neoplasms are targeted as a preventative measure to decrease the future risk that those neoplasms, often referred to as "in situ tumors," could acquire traits consistent with a malignant formation. One characteristic shared between all neoplasms, regardless of their potential to cause cancer, is a population of rapidly dividing cells. Therefore, to remove neoplasms from the host, the device is implanted in the area of the tumor, either in or around the cell mass, where one bioactive composition containing adhesive compounds, listed above for mammalian cells, mediates binding of tumor tissue to the scaffold, and any number of additional bioactive compositions comprising compounds or drugs with means to prevent or arrest cell division contact the captured cells in situ or diffuse from the scaffold composition into the surrounding tissue. Exemplary compounds with means to slow or retard the division of cells within a neoplasm include, but are not limited to, Dacarbazine/DTIC, Fluorouracil/5-FU, Fludarabine, Gemcitabine, Trastuzumab/Herceptin, Hydroxyurea/Hydrea, Idarubicin, Ifosfamide, Irinotecan, Cladribine/Leustatin, Mercaptopurine/Purinethol/6-MP, Methotrexate, Mithramycin/Plicamycin, Mitomycin, Mitoxanthrone/Novatrone, Navelbine/Vinorelbine, Nitrogen Mustard, Rituxan, Paclitaxel/Taxol, Docetaxel/Taxotere, Topotecan, Velban/Vinblastine, Vincristine, or Etoposide/VP-16 are incorporated, alone or in any combination thereof, into a bioactive composition within devices used for reversal of tumor formation. Cancers for which the device is used as a treatment or preventative measure at any point in the life span of the subject include, but are not limited to, acute lymphoblastic leukemia, acute myeloid leukemia, adrenocortical carcinoma, AIDS-related cancer, AIDS-related lymphoma, anal, appendix, cerebellar astrocytoma, cerebral astrocytoma, basal cell carcinoma, bile duct, bladder, one, osteosarcoma, malignant fibrous histiocytoma, brain stem glioma, brain, malignant glioma, ependymoma brain, medulloblastoma, supratentorial primitive neuroectodermal tumor, visual pathway and hypothalamic glioma, breast, bronchial adenomas, bronchial carcinoids, Burkitt's lymphoma, carcinoid tumor, gastrointestinal carcinoid tumor, carcinoma of unknown primary, central nervous system lymphoma, cervical, chronic lymphoid leukemia, chronic myelogenous leukemia, chronic myeloproliferative disorders, colon, colorectal, cutaneous T-cell lymphoma, mycosis fungoides, Sezary syndrome, endometrial, ependymoma, esophageal, Ewing's family of tumors, extracranial germ cell tumor, extragonadal germ cell tumor, extrahepatic bile duct, interocular melanoma, retinoblastoma, eye, gallbladder, gastric (stomach), gastrointestinal carcinoid tumor, gastrointestinal stromal tumor, ovarian germ cell tumor, germ cell tumor, gestational trophoblastic tumor, glioma, hairy cell leukemia, head, neck, hepatocellular, Hodgkin's lymphoma, hypopharangeal, islet cell carcinoma (endocrine pancreas), Kaposi's sarcoma, kidney (renal cell), kidney, laryngeal, lip and oral cavity, liver, lung (small cell), lung (non-small cell), Non-Hodgkin's lymphoma, Waldenstrom's macroglobulinemia, melanoma, merkel cell carcinoma, mesothelioma, metastatic squamous neck cancer with occult primary, mouth, multiple endocrine neoplasia syndrome, multiple myeloma, plasma cell neoplasm, myelodysplastic syndromes, myeloproliferative diseases, nasal cavity, paranasal sinus, nasopharyngeal, neuroblastoma, oral, oral cavity, oropharyngeal, ovarian, ovarian epithelial, ovarian low malignant potential tumor, pancreatic, parathyroid, penile, pharyngeal, pheochromocytoma, pineoblastoma, pituitary, pleuropulminary blastoma, prostate, rectal, renal pelvis and uterer, transitional cell cancer, rhabdomyosarcoma, salivary gland, soft tissue sarcoma, uterine sarcoma, skin (non-melanoma), small intestine, squamous cell carcinoma, T-cell lymphoma, testicular, throat, thymoma, thymoma carcinoma, thymic carcinoma, thyroid, unknown primary site cancer, unknown primary site carcinoma, urethral, uterine, vaginal, vulvar, or Wilm's tumor.

To prevent metastatic cells from escaping their primary tumor sites and disseminating to remote anatomical locations, one or more device(s) is implanted in or around malignant neoplasms. A bioactive composition is incorporated into or onto the scaffold composition, e.g. the scaffold not only contains cell-death-inducing agents, but also anti-metastatic compounds. Tumor cells that are preparing to enter the blood stream express cytokine receptors through which cytokines or chemokines provide migrational encouragement and instructions. Thus, bioactive compositions with means to retard or arrest metastasis include, but are not limited to, the following inhibitors of chemokine receptor activity: AMD3100, T22, TN14003, T140, TC14012, 4F-bTE, BX-471, Met-CCL5, TAK779, TAK220. By inhibiting chemokine receptor function, the preceding compounds prevent tumor cells from reacting to pro-metastatic or migratory cues present in their environment.

To capture mobile or circulating cancer cells which have broken free of their primary tumor formations, the device is administered systemically wherein it circulates in the blood, gastrointestinal tract, lymphatic fluid, or cerebral spinal fluid, and adheres and traps cancer cells by adhering to surface proteins unique to metastatic cell lines. Upon capturing these cells, the device is either used as a diagnostic tool, collected to identify the captured cells and determine the site of the primary tumor and metastasis. Alternatively, the device is used as a treatment method, and therefore, not collected, but rather a bioactive composition is incorporated within the device to eliminate the captured cell population. When the device is used to trap and kill metastatic cancer cells, and does not require collection, the scaffold composition degrades or is physically removed from the body, e.g. surgically collected. Alternatively, the device is used as an arterial stent. In this embodiment, the device is implanted and acts as a sieve, allowing all cell types to pass through, except for metastatic cancer cells that are captured by incorporating into the scaffold composition a bioactive composition with means to specifically adhere these cells. Upon contacting the stent device, captured cells are either instructed by either the flow dynamics inside of the scaffold or by a second bioactive composition to either enter an inside chamber where these cells die, or the captured cells are killed by direct interaction with a component of a second bioactive composition incorporated into the framework of the stent. Finally, a combination of these mechanisms is used to trap and kill metastatic cancer cells that either contact the framework or inner chambers of the scaffold composition. Furthermore, the bioactive compositions incorporated into either a mobile device or stent-like device can be altered to specifically adhere cells that contribute to forms of leukemia and lymphoma.

Autoimmune disease can be prevented, managed, or treated using the device. For this purpose the device is administered either locally or systemically and incorporated with a bioactive composition with means to irreversibly adhere immune cells predisposed to recognize self-antigens as "foreign," and in response to these antigens, signal to or recruit other immune cells, proliferate, or attack host tissues. A bioactive composition is incorporated into the scaffold composition that includes self-antigens, isolated from tissue samples taken from the subject, to target autoimmune cells, as well as, adhesive proteins to bind those immune cells, and signaling proteins to either induce cell death or prevent further immune responses. Ultimately, the device captures autoimmune cells by providing an alternative target for these immune cells as a way to competitively inhibit host antigen binding.

The device targets, captures, and eliminates malfunctioning host cells that cause damage to the subject by means of failing to properly perform a given function or by accumulating within the host, interrupting the function of healthy cells. For example, the device is used to preemptively capture and remove clot-forming red blood cells as a direct result of Sickle Cell Disease. Individuals with this condition express an abnormal form of hemoglobin, called hemoglobin S (named for hemoglobin "sickle"), on the surface of red blood cells. The presence of hemoglobin S induces several morphological changes: red blood cells devolve from soft, round cells that can fit through small-diameter vessels into hardened, sickle-shaped cells, which accumulate at points along the circulatory path, ultimately decreasing the flow of blood to nearby tissues. Moreover, blood cells that express hemoglobin S have a significantly shorter life-span than cells that express the wild type form. The device is administered intravenously to a subject as either a mobile device, or an arterial stent, both of which filter blood. Sickle cells are identified and trapped either by virtue of their altered morphology or by binding to hemoglobin S, thereby adhering these cells to the scaffold composition. Following their capture, sickle cells are induced to die prematurely via pro-apoptotic ligands or they are engulfed by phagocytic cells belonging to a bioactive composition. Both methods of sickle cell elimination occur within the confines of the scaffold composition.

The device is used to aid in the treatment of peripheral and central nerve injury. When a nerve is transected, such that the axons of nerve cells comprising the nerve bundle are severed, supporting cells, called glial cells, respond by forming a "glial scar" at the site of injury. The formation of this scar prevents the axon from regenerating by creating a physically impenetrable barrier between the cell's body and its synaptic targets. To prevent the glial scar from forming, the device is placed at the site of nerve transaction and throughout the surrounding tissue wherein bioactive compositions incorporated throughout the device adhere glial cells to the scaffold composition, capturing them, and/or eliminating them, in order to prevent their migration to or proliferation at the site of injury. When used to treat injuries sustained to the central nervous system, in which nerve regeneration is also chemically prohibited, bioactive compositions incorporated into the scaffold composition further comprise compounds with means to chelate anti-regeneration ligands (such as, Nogo), block anti-regeneration receptors (the Nogo receptor, Nogo-R), and those compounds, such as growth factors, with means to promote axon elongation. Bioactive compositions with means to stimulate nerve growth and/or attenuate anti-regeneration cues are either bonded to the scaffold composition or allowed to diffuse into the surrounding tissue or space.

To eliminate organic accumulations, plaques, or waste products that impair host function, the device contains live cell types or compounds that degrade these undesirable compositions. Exemplary cell types that clear harmful debris or accumulations commonly belong to the immune system and include, but are not limited to, macrophages, neutrophils, or natural killer (NK) cells. These immune cells are engineered to specifically target cell populations when they are released from the scaffold composition, however, these cells also reside inside the device and clear debris from the scaffold composition as captured cell types are eliminated. The presence of these cells allows the device to continually trap cells. To activate resident phagocytic cells, adiponectin, a protein normally produced by adipocytes and known to facilitate phagocytosis by forming a bridge between dead cells and macrophages, is further incorporated into one or more of the bioactive composition(s).

Genetically-manipulated viruses that are engineered to specifically attack target cell populations are incorporated into one or more bioactive composition(s) of the devise. These engineered viruses either permanently reside within the confines of the scaffold composition or, alternatively, diffuse into surrounding tissues following implantation of the device, dependent upon the precision of their specificity and the physical characteristics of the device placement. For example, oncolytic viruses are engineered to specifically infect cancer cells either by modification of their coat protein specificity or by altering the genome of the virus to render it replication-incompetent in any cell type other than a cancer cell. Adenovirus and herpes simplex virus are often used to infect cancer cells and are included in the bioactive composition of the device. Alternatively, some oncolytic viral strains are specific for cancer cells either due to the increased susceptibility of most cancer cells, as in the case of rhabdovirus, or, as a result of their natural specificity, as in the case of poliovirus, which evolved to be a neuropathogen. Furthermore, these viruses kill tumor cells either by lysing the cell, which is a normal function of a virus, or by delivering pro-apoptotic and/or anti-angiogenic genes to induce cell death, which is a genetically engineered function of these viruses. To prevent the host immune system from recognizing engineered viruses and inducing a response that could eliminate them before they have executed their function, e.g. infect cancer cells, these viruses are coated with a polymer, such as polyethylene glycol, which serves as a shield to antibodies.

The device controls and directs the migration of cells through its structure. Chemical affinities are used to channel cells towards a specific area of contact or quarantine. For example, attraction and adhesion molecules are used to attract or retard the migration of cells, respectively. By varying the density and mixture of those bioactive substances, the device controls the specificity of capture and location of adhesion. The density and mixture of these bioactive substances is controlled by initial doping levels or concentration gradient of the substance, by embedding the bioactive substances in scaffold material with a known leaching rate, by release as the scaffold material degrades, by diffusion from an area of concentration, by interaction of precursor chemicals diffusing into an area, or by production/excretion of compositions by resident support cells. The physical or chemical structure of the scaffold also regulates the diffusion of bioactive agents through the device.

The device is composed of a biocompatible material. One of the most common embodiments of the device incorporates the extracellular matrix (ECM) as a component of one or more bioactive composition(s) in order to adhere a wide variety of foreign and host cell types. In this case, the ECM is chemically cross-linked to the scaffold composition. Regardless of the tissue of origin, ECM components generally include three general classes of macromolecules: collagens, proteoglycans/glycosaminoglycans (PG/GAG), and glycoproteins, e.g., fibronectin (FN), laminin, and thrombospondin. ECM components associate with molecules on the cell surface and mediate adhesion and/or motility. Preferably, the ECM component associated with the scaffold is a proteoglycan attachment peptide or cyclic peptide containing the amino acid sequence arginine-glycine-aspartic acid (RGD). Proteoglycan attachment peptides are selected from the group consisting of $G_4$RGDSP (SEQ ID NO: 1), XBBXBX (SEQ ID NO: 2), PRRARV (SEQ ID NO: 3), YEKPGSPPREVVPRPRPGV (SEQ ID NO: 4), RPSLAKKQRFRHRNRKGYRSQRGHSRGR (SEQ ID NO: 5), and RIQNLLKITNLRIKFVK (SEQ ID NO: 6), and cell attachment peptides are selected from the group consisting of RGD, RGDS (SEQ ID NO: 12), LDV, REDV (SEQ ID NO: 13), RGDV (SEQ ID NO: 14), LRGDN (SEQ ID NO: 7), IKVAV (SEQ ID NO: 8), YIGSR (SEQ ID NO: 9), PDSGR (SEQ ID NO: 10), RNIAEIIKDA (SEQ ID NO: 11), RGDT (SEQ ID NO: 15), DGEA (SEQ ID NO: 16), and VTXG (SEQ ID NO: 17).

Components of the ECM, e.g., FN, laminin, and collagen, interact with the cell surface via the integrin family of receptors, a group of divalent cation-dependent cell surface glycoproteins that mediate cellular recognition and adhesion to components of the ECM and to other cells. Ligands recognized by integrins typically contain an RGD amino acid sequence that is expressed in many ECM proteins. Exemplary molecules that mediate cell adhesion and/or movement include FN, laminin, collagen, thrombospondin 1, vitronectin, elastin, tenascin, aggrecan, agrin, bone sialoprotein, cartilage matrix protein, fibronogen, fibrin, fibulin, mucins, entactin, osteopontin, plasminogen, restrictin, serglycin, SPARC/osteonectin, versican, von Willebrand Factor, polysaccharide heparin sulfate, cell adhesion molecules including connexins, selectins, collagen, RGD (Arg-Gly-Asp) and YIGSR (Tyr-Ile-Gly-Ser-Arg) (SEQ ID NO: 9) peptides, glycosaminoglycans (GAGs), hyaluronic acid (HA), integrins, selectins, cadherins and members of the immunoglobulin superfamily. Carbohydrate ligands of the ECM include the polysaccharides hyaluronic acid, and chondroitin-6-sulfate.

To create a multifunctional device, a plurality of bioactive compositions are covalently linked to the scaffold composition, keeping these compositions relatively immobilized in or on the scaffold composition. In other cases, additional bioactive compositions are noncovalently associated with the scaffold. Noncovalent bonds are generally one to three orders of magnitude weaker than covalent bonds permitting diffusion of the factor within the compartments of the device, and ultimately, out of the scaffold and into surrounding tissues. Noncovalent bonds include electrostatic, hydrogen, van der Waals, π aromatic, and hydrophobic interactions.

The scaffold composition is also contacted with a second bioactive composition. The second bioactive composition is sometimes non-covalently associated with the scaffold composition to yield a layered scaffold, i.e., a scaffold composition that includes one or more bioactive substances. The application of contacting of the scaffold composition with a second bioactive composition is optionally repeated to yield a plurality of scaffold structures, e.g., each of the contacting steps is characterized by a different amount of the second bioactive composition to yield a gradient of the second bioactive composition in the scaffold device. Rather than altering the amount of composition, subsequent contacting steps involve a different bioactive composition, i.e., a third, fourth, fifth, sixth . . . , composition or mixture of compositions, that is distinguished from the prior compositions or mixtures of prior doping steps by the structure or chemical formula of the factor(s). The layers, or components of the scaffold form a gradient to lure undesirable cells into the device to one another and/or insertion of semi-permeable, permeable, or impermeable membranes within or at one or more boundaries of the device to further controls/regulate the locomotion of cells or bioactive compositions into the scaffold to trap the cells therein, as well as the elimination of resident cell populations.

The scaffold composition can be constructed using a variety of materials that will be chosen according to its desired function. In all cases, the scaffold composition is biocompatible, meaning that the scaffold composition itself does not induce damage or activate the host immune system. The composition is bio-degradable/erodable or resistant to breakdown in the body. Relatively permanent (degradation resistant) scaffold compositions include metals and some polymers such as silk.

The scaffold composition is used for a variety of functions for which one or more of the bioactive compositions destroy (s) the captured cell population. Therefore, the scaffold itself does not need to exist indefinitely either internal or external to the host, and is composed of a biodegradable material. Breakdown of the scaffold composition as a result of any or all of the following events: the captured cells release one or more corrosive compound(s), the local host environment where the scaffold resides contains one or more corrosive compound(s), the process of eliminating the captured cells produces one or more corrosive compound(s), the bioactive composition itself compromises the structural integrity of the scaffold, the scaffold disassembles upon collection. In one example, cells mediate degradation of the scaffold matrix, i.e., the scaffold composition is enzymatically digested by a composition elicited by a resident cell. In this case, polymer main chains or cross-links contain compositions, e.g., oligopeptides, that are substrates for collagenase or plasmin, or other enzymes produced by within or adjacent to the scaffold.

For some applications, the scaffold composition preferably degrades at a predetermined rate based on a physical parameter selected from the group consisting of temperature, pH, hydration status, and porosity, the cross-link density, type, and chemistry or the susceptibility of main chain linkages to degradation or it degrades at a predetermined rate based on a ratio of chemical polymers. For example, a high molecular weight polymer comprised of solely lactide degrades over a period of years, e.g., 1-2 years, while a low molecular weight polymer comprised of a 50:50 mixture of lactide and glycolide degrades in a matter of weeks, e.g., 1, 2, 3, 4, 6, 10 weeks. A calcium cross-linked gels composed of high molecular weight, high guluronic acid alginate degrade over several months (1, 2, 4, 6, 8, 10, 12 months) to years (1, 2, 5 years) in vivo, while a gel comprised of low molecular weight alginate, and/or alginate that has been partially oxidized, will degrade in a matter of weeks.

Exemplary scaffold compositions include polylactic acid, polyglycolic acid, PLGA polymers, alginates and alginate derivatives, gelatin, collagen, fibrin, hyaluronic acid, laminin rich gels, agarose, natural and synthetic polysaccharides, polyamino acids, polypeptides, polyesters, polyanhydrides, polyphosphazines, poly(vinyl alcohols), poly(alkylene oxides), poly(allylamines)(PAM), poly(acrylates), modified styrene polymers, pluronic polyols, polyoxamers, poly(uronic acids), poly(vinylpyrrolidone) and copolymers or graft copolymers of any of the above. One preferred scaffold composition includes an RGD-modified alginate.

For some applications, porosity of the scaffold composition influences selectivity of the cells captured by or permitted through the device. Pores are nanoporous, microporous, or macroporous. For example, the diameter of nanopores are less than about 10 nm; micropore are in the range of about 100 nm-20 μm in diameter; and, macropores are greater than about 20 μm (preferably greater than about 100 μm and even more preferably greater than about 400 μm). In one example, the scaffold is macroporous with aligned pores of about 400-500 μm in diameter.

The devices are manufactured in their entirety in vitro. Furthermore the devices can be assembled around or in contact with engineered cultured cells or viruses with means to attract, adhere, or eliminate captured target cells, in order to produce a scaffold and bioactive composition combination that includes living or dead cells. Alternatively, the device is manufactured in two or more (3, 4, 5, 6, . . . 10 or more) stages in which one layer or compartment is made and coated with bioactive composition followed by the construction of a second, third, fourth or more layers, which are in turn coated with bioactive material in sequence. Each layer or compartment is identical to the others or distinguished from one another by the number, genotype, or phenotype of the seed cell population as well as distinct chemical, physical and biological properties of the scaffold or bioactive composition.

Therapeutic applications of the device include diagnosis of infection by microorganisms, or the discovery and diagnosis of diseased host tissues that contribute to sickle cell disease, leukemia, metastatic cancer, autoimmune conditions, or inflammatory disease. Moreover, this device is used as a diagnostic tool to capture and identify cancer cells that have metastasized potentially from multiple primary tumors, thereby eliminating the need for multiple biopsies or more invasive surgical options. Alternatively, this devise is used as a medical treatment to eliminate microorganisms, malignant neoplasms, leukemia, lymphoma, arterial blockages, adipose tissue, inflammation, glial scars, and protein deposits. Furthermore, this devise can be used for preventative medicine to assess exposure to microorganisms, eliminate benign neoplasms, eliminate immune cells that activate to self-antigens, as well as prevent arterial build-up or glial scaring following nerve damage.

Other features and advantages of the invention will be apparent from the following description of the preferred embodiments thereof, and from the claims. References cited are hereby incorporated by reference.

DETAILED DESCRIPTION OF THE INVENTION

The device contains a scaffold composition incorporated with one or more bioactive compositions. The most fundamental functions of the device are capturing and eliminating target cells from a host organism. In this case, the "host" is any mammalian subject and the term "host cell" describes any cell that is recognized by a healthy immune system as displaying self-antigens. Alternatively, a "foreign cell" is meant to describe any cell that is recognized by a healthy immune system as displaying non-self, or foreign, surface antigens as well as any cell that was not born, or generated, within the host organism. The term "undesirable" cell is meant to describe any cell that increases the risk or susceptibility of the host to infection or disease, or any cell that decreases the ability of the host to thrive. The term "scaffold composition" is meant to describe a biocompatible, biodegradable or non-biodegradable frame, used to deliver a bioactive composition to a particular location of the body, or to create a physical niche into or onto which targeted cell types accumulate and, by this act, are destroyed or removed from the context of the host body. The term, "bioactive composition" is meant to describe any combination of molecules, compounds, proteins, or cell types having means to alter the behavior of the target cell type. The bioactive compositions used within the invented device either remain incorporated with the scaffold composition, or they may diffuse from the scaffold structure to contact surrounding target tissues.

Resident cells, incorporated into a bioactive composition prior to administering the device to a subject, including immune cells and viruses, are optionally genetically manipulated by the introduction of exogenous genetic sequences or the inactivation or modification of endogenous sequences. For example, recombinant genes are introduced to cause the cells to encode or make proteins that are otherwise lacking in the host or target tissue. Production of scarce but desirable proteins (in the context of certain tissues) is augmented by transplanting genetically engineered cells. General mammalian cell culture techniques, cell lines, and cell culture systems are described in Doyle, A., Griffiths, J. B., Newell, D. G., (eds.) *Cell and Tissue Culture: Laboratory Procedures*, Wiley, 1998, the contents of which are incorporated herein by reference.

Scaffold Compositions and Architecture

Components of the scaffolds are organized in a variety of geometric shapes (e.g., beads, pellets), niches, planar layers (e.g., thin sheets). For example, multi-component scaffolds are constructed in concentric layers each of which is characterized by different physical qualities (% polymer, % cross-linking of polymer, chemical composition of scaffold, pore size, porosity, and pore architecture, stiffness, toughness, ductility, viscoelasticity, and or composition of bioactive substances such as growth factors, homing/migration factors, differentiation factors. Each niche has a specific effect on a cell population, e.g., promoting or inhibiting a specific cellular function, attraction, adhesion, elaboration of secreted factors or enzymes, or induction of cell death. Cells implanted within the scaffold prior to administration of the device to a subject are engineered to target specific cell populations only, and permitted to migrate out of the scaffold to eliminate a target tissue. For example, engineered viruses and activated macrophages are released from the scaffold composition to either infect target cells or clear debris from the surrounding tissue. For some purposes, the device acts locally, and is therefore placed or transplanted into, on, or proximal to a target tissue, wherein that target tissue resides either internal or external (skin surfaces) to the body. Alternatively, the device acts systemically and is therefore introduced into the gastrointestinal tract, blood supply, lymphatic fluid, or cerebral spinal fluid. Devices are introduced into or onto a bodily tissue using a variety of known methods and tools, e.g., gelatin-coated pill, spoon, tweezers or graspers, hypodermic needle, endoscopic manipulator, endo- or trans-vascular-catheter, stereotaxic needle, snake device, organ-surface-crawling robot (United States Patent Application 20050154376; Ota et al., 2006, Innovations 1:227-231), minimally invasive surgical devices, surgical implantation tools, and transdermal patches. Devices can also be assembled in place, for example by sequentially injecting or inserting matrix materials. Scaffold devices are optionally recharged with cells or with bioactive compounds.

A scaffold or scaffold device is the physical structure upon which or into which cells associate or attach, and a scaffold composition is the material from which the structure is made. For example, scaffold compositions include biodegradable or permanent materials such as those listed below. The mechanical characteristics of the scaffold vary according to the application or tissue type for which elimination is sought. In the series of experiments described in the examples, a polymer formulation consisting of poly(lactide-co-glycolide) (PLG) was used. Other preferred polymers include but are not limited to poly(lactide)s, poly(glycolide)s, poly(lactic acid)s, poly(glycolic acid)s, polyanhydrides, polyorthoesters, polyetheresters, polycaprolactones, polyesteramides, polycarbonates, polycyanoacrylates, polyurethanes, polyacrylates, and blends or copolymers of the above. A scaffold or scaffold device is biodegradable (e.g., collagen, alginates, polysaccharides, polyethylene glycol (PEG), poly(glycolide) (PGA), poly(L-lactide) (PLA), or poly(lactide-co-glycolide) (PLGA) or permanent (e.g., silk).

In one embodiment, the scaffold or scaffold device comprises a biocompatible polymer matrix that may optionally be biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-.epsilon.-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers. In another embodiment, the scaffolds may be fabricated from a variety of synthetic polymers and naturally-occurring polymers such as, but not limited to, collagen, fibrin, hyaluronic acid, agarose, and laminin-rich gels. In the case of biodegradable structures, the composition is degraded by physical or chemical action, e.g., level of hydration, heat or ion exchange or by cellular action, e.g., elaboration of enzyme, peptides, or other compounds by nearby or resident cells. The consistency varies from a soft/pliable (e.g., a gel) to glassy, rubbery, brittle, tough, elastic, stiff. The structures contain pores, which are nanoporous, microporous, or macroporous, and the pattern of the pores is optionally homogeneous, heterogeneous, aligned, repeating, or random.

Alginates are versatile polysaccharide based polymers that may be formulated for specific applications by controlling the molecular weight, rate of degradation and method of scaffold formation. Coupling reactions can be used to covalently attach bioactive epitopes, such as the cell adhesion sequence RGD to the polymer backbone. Alginate polymers are formed into a variety of scaffold types. Injectable hydrogels can be formed from low MW alginate solutions upon addition of a cross-linking agents, such as calcium ions, while macroporous scaffolds are formed by lyophilization of high MW alginate discs. Differences in scaffold formulation control the kinetics of scaffold degradation. Release rates of morphogens or other bioactive substances from alginate scaffolds is controlled by scaffold formulation to present morphogens in a spatially and temporally controlled manner. This controlled release not only eliminates systemic side effects and the need for multiple injections, but can be used to create a microenvironment that activates host cells at the implant site and transplanted cells seeded onto a scaffold.

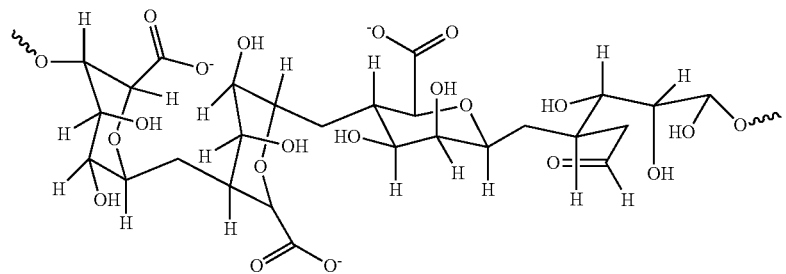

Partially oxidized alginate

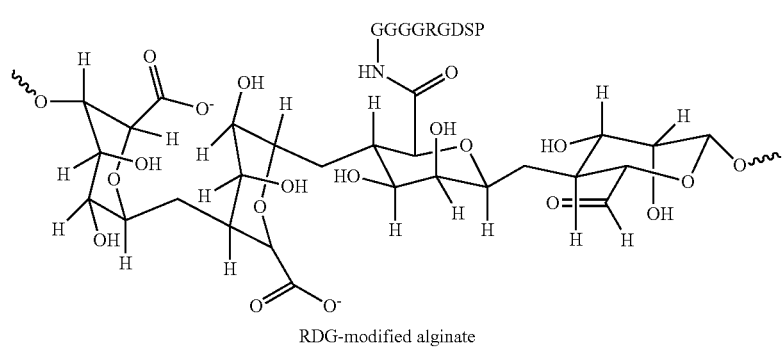

RDG-modified alginate
(SEQ ID NO: 1)

The scaffold comprises a biocompatible polymer matrix that is optionally biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-epsilon, poly-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers.

Scaffold Fabrication

Scaffolds are fabricated from a variety of synthetic polymers and naturally-occurring polymers such as, but not limited to, collagen, fibrin, hyaluronic acid, agarose, and laminin-rich gels. One preferred material for the hydrogel is alginate or modified alginate material. Alginate molecules are comprised of (1-4)-linked β-D-mannuronic acid (M units) and α L-guluronic acid (G units) monomers, which can vary in proportion and sequential distribution along the polymer chain. Alginate polysaccharides are polyelectrolyte systems which have a strong affinity for divalent cations (e.g. $Ca^{+2}$, $Mg^{+2}$, $Ba^{+2}$) and form stable hydrogels when exposed to these molecules. See Martinsen A., et al., Biotech. & Bioeng., 33 (1989) 79-89.) For example, calcium cross-linked alginate hydrogels are useful as a matrix for other cell types. cross-linked alginate hydrogels have been used in many biomedical applications, including materials for dental impressions (Hanks C. T., et al., Restorative Dental Materials; Craig, R. G., ed., Ninth Edition, Mosby (1993)), wound dressings (Matthew I. R. et al., Biomaterials, 16 (1995) 265-274), an injectable delivery medium for chondrocyte transplantation (Atala A., et al., J Urology, 152 (1994) 641-643), and an immobilization matrix for living cells (Smidsrod O., et al, TIBTECH 8 (1990) 71-78).

An exemplary device utilizes an alginate or other polysaccharide of a relatively low molecular weight, preferably of size which, after dissolution, is at the renal threshold for clearance by humans, e.g., the alginate or polysaccharide is reduced to a molecular weight of 1000 to 80,000 daltons. Preferably, the molecular mass is 1000 to 60,000 daltons, particularly preferably 1000 to 50,000 daltons. It is also useful to use an alginate material of high guluronate content since the guluronate units, as opposed to the mannuronate units, provide sites for ionic cross-linking through divalent cations to gel the polymer. U.S. Pat. No. 6,642,363, incorporated herein by reference discloses methods for making and using polymers containing polysaccharides such as alginates or modified alginates.

Useful polysaccharides other than alginates include agarose and microbial polysaccharides such as those listed in the table below.

| Polysaccharide Scaffold Compositions | |
|---|---|
| Polymers[a] | Structure |
| Fungal | |
| Pullulan (N) | 1,4-; 1,6-α-D-Glucan |
| Scleroglucan (N) | 1,3; 1,6-α-D-Glucan |
| Chitin (N) | 1,4-β-D-Acetyl Glucosamine |
| Chitosan (C) | 1,4-β.-D-N-Glucosamine |
| Elsinan (N) | 1,4-; 1,3-α-D-Glucan |
| Bacterial | |
| Xanthan gum (A) | 1,4-β.-D-Glucan with D-mannose; D-glucuronic Acid as side groups |
| Curdlan (N) | 1,3-β.-D-Glucan (with branching) |
| Dextran (N) | 1,6-α-D-Glucan with some 1,2; 1,3-; 1,4-α-linkages |
| Gellan (A) | 1,4-β.-D-Glucan with rhamose, D-glucuronic acid |
| Levan (N) | 2,6-β-D-Fructan with some β-2,1-branching |
| Emulsan (A) | Lipoheteropolysaccharide |
| Cellulose (N) | 1,4-β-D-Glucan |

[a]N—neutral, A = anionic and C = cationic.

The scaffolds of the invention are porous or non-porous. For example, the scaffolds are nanoporous having a diameter of less than about 10 nm; microporous wherein the diameter of the pores are preferably in the range of about 100 nm-20 μm; or macroporous wherein the diameter of the pores are greater than about 20 μm, more preferably greater than about 100 μm and even more preferably greater than about 400 μm. In one example, the scaffold is macroporous with aligned pores of about 400-500 μm in diameter. The preparation of polymer matrices having the desired pore sizes and pore alignments are described in the Examples. Other methods of preparing porous hydrogel products are known in the art. (U.S. Pat. No. 6,511,650 incorporated herein by reference).

Bioactive Compositions

The device includes one or more bioactive compositions. Bioactive compositions are purified naturally-occurring, synthetically produced, or recombinant compounds, e.g., polypeptides, nucleic acids, small molecules, or other agents. The compositions described herein are purified. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

The bioactive composition affects cell mobility and survival by inducing changes in the surface protein expression or interaction, or intracellular signaling of a cell, by restricting its access to environmental cues, or by contacting a cell with a modified cell type with means to induce cell death, compromise the structural integrity of the target cell, or engulf the target cell. For example, at least one cell adhesion molecule is incorporated into or onto the polymer matrix. Such molecules are incorporated into the polymer matrix prior to polymerization of the matrix or after polymerization of the matrix. Examples of cell adhesion molecules include but are not limited to peptides, proteins and polysaccharides. More specifically, cell adhesion molecules include fibronectin, laminin, collagen, thrombospondin 1, vitronectin, elastin, tenascin, aggrecan, agrin, bone sialoprotein, cartilage matrix protein, fibronogen, fibrin, fibulin, mucins, entactin, osteopontin, plasminogen, restrictin, serglycin, SPARC/osteonectin, versican, von Willebrand Factor, polysaccharide heparin sulfate, connexins, collagen, RGD (Arg-Gly-Asp) and YIGSR (Tyr-Ile-Gly-Ser-Arg) (SEQ ID NO: 9) peptides and cyclic peptides, glycosaminoglycans (GAGs), hyaluronic acid (HA), condroitin-6-sulfate, integrin ligands, selectins, cadherins and members of the immunoglobulin superfamily. Other examples include neural cell adhesion molecules (NCAMs), intercellular adhesion molecules (ICAMs), vascular cell adhesion molecule (VCAM-1), platelet-endothelial cell adhesion molecule (PECAM-1), L1, and CHL1.

Particularly preferred cell adhesion molecules of the invention are peptides or cyclic peptides containing the amino acid sequence arginine-glycine-aspartic acid (RGD) which is known as a cell attachment ligand and found in various natural extracellular matrix molecules. A polymer matrix with such a modification provides cell adhesion properties to the scaffold of the invention, and sustains long-term survival of mammalian cell systems, as well as supporting cell growth and differentiation.

Examples of some of these molecules and their function are shown in the following table.

ECM Proteins and peptides and role in cell function

| Protein | Sequence | Seq. ID No: | Role |
|---|---|---|---|
| Fibronectin | RGDS | 12 | Adhesion |
| | LDV | | Adhesion |
| | REDV | 13 | Adhesion |
| Vitronectin | RGDV | 14 | Adhesion |
| Laminin A | LRGDN | 7 | Adhesion |
| | IKVAV | 8 | Neurite extension |
| Laminin B1 | YIGSR | 9 | Adhesion of many cells, via 67 kD laminin receptor |
| | PDSGR | 10 | Adhesion |
| Laminin B2 | RNIAEIIKDA | 11 | Neurite extension |
| Collagen 1 | RGDT | 15 | Adhesion of most cells |
| | DGEA | 16 | Adhesion of platelets, other cells |
| Thrombospondin | RGD | | Adhesion of most cells |
| | VTXG | 17 | Adhesion of platelets |

Hubbell, J A (1995): Biomaterials in tissue engineering.
Bio/Technology 13: 565-576. One-letter abbreviations of amino acids are used, X stands for any amino acid.

Additional examples of suitable cell adhesion molecules are shown below.

Amino acid sequences specific for proteoglycan binding from extracellular matrix proteins

| SEQUENCE | SEQ. ID. NO. | PROTEIN |
|---|---|---|
| XBBXBX* | 2 | Consensus |
| PRRARV | 3 | Fibronectin |
| YEKPGSPPREVVPRPRPGV | 4 | Fibronectin |
| RPSLAKKQRFRHRNRKGYRSQRGHSRGR | 5 | Vitronectin |
| RIQNLLKITNLRIKFVK | 6 | Laminin |

Coupling of the cell adhesion molecules to the polymer matrix is accomplished using synthetic methods which are in general known to one of ordinary skill in the art and are described in the examples. Approaches to coupling of peptides to polymers are discussed in Hirano and Mooney, *Advanced Materials*, p. 17-25 (2004). Other useful bonding chemistries include those discussed in Hermanson, *Bioconjugate Techniques*, p. 152-185 (1996), particularly by use of carbodiimide couplers, DCC and DIC (Woodward's Reagent K). Since many of the cell adhesion molecules are peptides, they contain a terminal amine group for such bonding. The amide bond formation is preferably catalyzed by 1-ethyl-3-(3-dimethylaminopropyl) carbodiimide (EDC), which is a water soluble enzyme commonly used in peptide synthesis. The density of cell adhesion ligands, a critical regulator of cellular phenotype following adhesion to a biomaterial. (Massia and Hubbell, *J. Cell Biol.* 114:1089-1100, 1991; Mooney et al., J. Cell Phys. 151:497-505, 1992; and Hansen et al., *Mol. Biol. Cell* 5:967-975, 1994) can be readily varied over a 5-order of magnitude density range.

Device Construction

The scaffold structure is constructed out of a number of different rigid, semi-rigid, flexible, gel, self-assembling, liquid crystalline, or fluid compositions such as peptide polymers, polysaccharides, synthetic polymers, hydrogel materials, ceramics (e.g., calcium phosphate or hydroxyapatite), proteins, glycoproteins, proteoglycans, metals and metal alloys. The compositions are assembled into cell scaffold structures using methods known in the art, e.g., injection molding, lyophilization of preformed structures, printing, self-assembly, phase inversion, solvent casting, melt processing, gas foaming, fiber forming/processing, particulate leaching or a combination thereof. The assembled devices are then implanted or administered to the body of a subject.

The device is assembled in vivo in several ways. The scaffold is made from a gelling material, which is introduced into the body in its ungelled form where it gels in situ. Exemplary methods of delivering device components to a site at which assembly occurs include injection through a needle or other extrusion tool, spraying, painting, or methods of deposit at a tissue site, e.g., delivery using an application device inserted through a cannula. In one example, the ungelled or unformed scaffold material is mixed with bioactive substances and/or cells prior to introduction into the body or while it is introduced. The resultant in vivo/in situ assembled scaffold contains a mixture of these substances and/or cells.

In situ assembly of the scaffold occurs as a result of spontaneous association of polymers or from synergistically or chemically catalyzed polymerization. Synergistic or chemical catalysis is initiated by a number of endogenous factors or conditions at or near the assembly site, e.g., body temperature, ions or pH in the body, or by exogenous factors or conditions supplied by the operator to the assembly site, e.g., photons, heat, electrical, sound, or other radiation directed at the ungelled material after it has been introduced. The energy is directed at the scaffold material by a radiation beam or through a heat or light conductor, such as a wire or fiber optic cable or an ultrasonic transducer. Alternatively, a shear-thinning material, such as an ampliphile, is used which re-cross links after the shear force exerted upon it, for example by its passage through a needle, has been relieved.

Suitable hydrogels for both in vivo and ex vivo assembly of scaffold devices are well known in the art and described, e.g., in Lee et al., 2001, Chem. Rev. 7:1869-1879. The peptide amphiphile approach to self-assembly assembly is described, e.g., in Hartgerink et al., 2002, Proc. Natl. Acad. Sci. U.S.A 99:5133-5138. A method for reversible gellation following shear thinning is exemplified in Lee et al., 2003, Adv. Mat. 15:1828-1832

A multiple compartment device is assembled in vivo by applying sequential layers of similarly or differentially doped gel or other scaffold material to the target site. For example, the device is formed by sequentially injecting the next, inner layer into the center of the previously injected material using a needle, forming concentric spheroids. Non-concentric compartments are formed by injecting material into different locations in a previously injected layer. A multi-headed injection device extrudes compartments in parallel and simultaneously. The layers are made of similar or different scaffolding compositions differentially doped with bioactive substances and different cell types. Alternatively, compartments self-organize based on their hydrophilic/phobic characteristics or on secondary interactions within each compartment.

Compartmentalized Device

In certain situations, a device containing compartments with distinct chemical and/or physical properties is useful. Such a configuration is particularly useful when separating quarantined cell populations undergoing elimination from the outside tissue. For instance, the process or byproduct of cell destruction could interfere with the ability of non-target cells to pass through the device and remain unaffected. Therefore, it is advantageous to have multiple compartments, some of which serve to contain harmful agents or cells from gaining access to healthy tissue. Alternatively, the device captures multiple undesirable cell types and sorts them into different chambers of the device where these cell populations contact bioactive compositions containing unique combinations of attractive, adhesive, and destructive agents.

A compartmentalized device is designed and fabricated using different compositions or concentrations of compositions for each compartment. For example, and engineered cell population with means to induce death of target cells is encapsulated within hydrogels, using standard encapsulation techniques (e.g., alginate microbead formation). This first hydrogel contains factors required to maintain and contact these engineered cells with target cells, either by their covalent coupling to the polymer forming the gel or by their slow and sustained release from the gel. This compartment is then coated with a second layer of gel (e.g., double layered alginate microbeads) that contains factors that do not support the survival of these engineered cells, but instead adhere target cells in order to expose them to the engineered population in a controlled manner. This second compartment is formed from the same material that contains distinct factors (e.g., attractive and/or adhesive ligands), the same material in a distinct form (e.g., varying mechanical properties or porosity), or a completely different material that provides appropriate chemical/physical properties.

Alternatively, the compartments are fabricated individually, and then adhered to each other (e.g., a "sandwich" with an inner compartment surrounded on one or all sides with the second compartment). This latter construction approach is accomplished using the intrinsic adhesiveness of each layer for the other, diffusion and interpenetration of polymer chains in each layer, polymerization or cross-linking of the second layer to the first, use of an adhesive (e.g., fibrin glue), or physical entrapment of one compartment in the other. The compartments self-assemble and interface appropriately, either in vitro or in vivo, depending on the presence of appropriate precursors (e.g., temperature sensitive oligopeptides, ionic strength sensitive oligopeptides, block polymers, cross-linkers and polymer chains (or combinations thereof), and precursors containing cell adhesion molecules that allow cell-controlled assembly). Multiple compartments are designed to capture and either contain or eliminate target cells appropriately. In addition, the device is designed to have a number of compartments, in which cells enter in parallel, in contrast to serially passing through all compartments. The different compartments each capture target cells induce cell death of the contained cells by a unique mechanism, and in this manner provide a means to either remove the same target cell type by a variety of methods or to remove multiple target cell types by unique methods most appropriate for each captured population. An individual with ordinary skill in the art of medicine and biomaterials can readily derive a number of potentially useful designs for a given starting cell type and desired daughter cell output.

Alternatively, the compartmentalized device is formed using a printing technology. Successive layers of a scaffold precursor doped with bioactive substances and/or cells is placed on a substrate then cross linked, for example by self-assembling chemistries. When the cross linking is controlled by chemical-, photo- or heat-catalyzed polymerization, the thickness and pattern of each layer is controlled by a masque, allowing complex three dimensional patterns to be built up when un-cross-linked precursor material is washed away after each catalyzation. (W T Brinkman et al., Photo-cross-linking of type 1 collagen gels in the presence of smooth muscle cells: mechanical properties, cell viability, and function. *Biomacromolecules,* 2003 July-August; 4(4): 890-895; W. Ryu et al., The construction of three-dimensional micro-fluidic scaffolds of biodegradable polymers by solvent vapor based bonding of micro-molded layers. *Biomaterials,* 2007 February; 28(6): 1174-1184; Wright, Paul K. (2001). 21*st Century manufacturing.* New Jersey: Prentice-Hall Inc.) Complex, multi-compartment layers are also built up using an inkjet device which "paints" different doped-scaffold precursors on different areas of the substrate. Julie Phillippi (Carnegie Mellon University) presentation at the annual meeting of the American Society for Cell Biology on Dec. 10, 2006; Print me a heart and a set of arteries, Aldhouse P., New Scientist 13 April 2006 Issue 2547 p 19; Replacement organs, hot off the press, C. Choi, New Scientist, 25 Jan. 2003, v2379. These layers are built-up into complex, three dimensional compartments. The device is also built using any of the following methods: Jetted Photopolymer, Selective Laser Sintering, Laminated Object Manufacturing, Fused Deposition Modeling, Single Jet Inkjet, Three Dimensional Printing, or Laminated Object Manufacturing.

Incorporation of Compositions into/onto a Scaffold Device

Bioactive substances that influence attraction, adhesion, and cell death are introduced into or onto the scaffold structures. Cell-cell adhesion molecules (cadherins, integrins, ALCAM, NCAM, proteases) are optionally added to the scaffold composition.

The release profiles of bioactive substances from scaffold devices is controlled by both diffusion and polymer degradation, the dose of the compound loaded in the system, and the composition of the polymer. Similarly, the range of action (tissue distribution) and duration of action, or spatiotemporal gradients of these substances are regulated by these variables. The diffusion and degradation of the factors in the tissue of interest is optionally regulated by chemically modifying the factors, or by an activity limiting factor of the substance itself, i.e., the half-life of radioisotope limits the duration of its emission into nearby tissue.

The bioactive substances are added to the scaffold compositions using known methods including surface absorption, physical immobilization, e.g., using a phase change to entrap the substance in the scaffold material. For example, a growth factor is mixed with the scaffold composition while it is in an aqueous or liquid phase, and after a change in environmental conditions (e.g., pH, temperature, ion concentration), the liquid gels or solidifies thereby entrapping the bioactive substance. Alternatively, covalent coupling, e.g., using alkylating or acylating agents, is used to provide a stable, long-term presentation of a bioactive substance on the scaffold in a defined conformation. Exemplary reagents for covalent coupling of such substances are provided in the table below.

| Methods to covalently couple peptides/proteins to polymers | | |
|---|---|---|
| Functional Group of Polymer | Coupling reagents and cross-linker | Reacting groups on proteins/peptides |
| —OH | Cyanogen bromide (CNBr) Cyanuric chloride 4-(4,6-Dimethoxy-1,3,5-triazin-2-yl)-4-methyl-morpholinium chloride (DMT-MM) | —NH$_2$ |
| —NH$_2$ | Diisocyanate compounds Diisothoncyanate compounds Glutaraldehyde Succinic anhydride | —NH$_2$ —OH |
| —NH$_2$ | Nitrous Acid Hydrazine + nitrous acid | —NH$_2$ —SH —Ph—OH |
| —NH$_2$ | Carbodiimide compounds (e.g., EDC, DCC)[a] DMT-MM | —COOH |
| —COOH | Thionyl chloride N-hydroxysuccinimide N-hydroxysulfosuccinimide + EDC | —NH$_2$ |
| —SH | Disulfide compound | —SH |

[a]EDC: 1-ethyl-3-(3-dimethylaminopropyl) carbodiimide hydrochloride; DCC: dicyclohexylcarbodiimide Bioactive substances are capable of attracting target cell types toward or into the device and adhering target cell types upon contact. Other preferred bioactive substances are capable inducing cell death of captured cells, or target cell types in close proximity of the device. Such bioactive substances are used alone or in combination to achieve the desired result.

EXAMPLES

Example 1: Collection and Removal of Microorganisms to Prevent, Diagnose, or Treat Infectious Disease Hosts exposed to or infected by invasive microorganisms such as viruses, bacteria, protozoa, fungi, or worms, typically do not present symptoms of infection immediately. By the time the host presents outward signs of an infection, ingested microorganisms have likely matured, multiplied, spread, or inflicted damage upon host tissues. The subject is identified as planning to be located in an environment characterized by the presence of such a pathogen or having recently been located in such an environment. The scaffold composition is administered to the host subject either prior to or following exposure to these microorganisms, wherein the device captures microorganism by filtration or specific adhesion proteins contained within a bioactive composition. When the device is administered very soon after exposure, the device eliminates microorganisms, and prevents the spread of infection. Alternatively, the device is administered and collected in order to identify the infectious agent to which the subject was exposed prior to the emergence of symptoms, providing a valuable head-start on diagnosing and treating future disease. Moreover, the scaffold is administered to non-human species residing in areas of suspected infestation in order to identify potential threats to humans living in nearby as a preventative measure.

The impact of this diagnostic innovation for microorganisms can only be fully appreciated in light of the number of microorganisms that can cause disease. Exemplary viral classes that infect human hosts include, but are not limited to: adenoviruses, herpesviruses, poxviruses, parvoviruses, papovaviruses, hepadnaviruses, orthomyxoviruses, paramyxoviruses, coronaviruses, picornaviruses, reoviruses, togaviruses, flaviviruses, arenaviruses, rhabdoviruses, and retroviruses. The common names for some of the diseases caused by the viral classes listed above include: smallpox, fifth disease, HPV, HBV, kidney disease, influenza, mumps, measles, subacute sclerosing panenephalitis, RSV, cold, poliomyelitis, hand-foot-and-mouth disease, nonspecific febrile illness, croup, bronchitis, pneumonia, hepatitis, pancreatitis, arthritis, diabetes, meningitis, encephalitis, paralysis, viral myocarditis, HAV, gastroenteritis, diarrhea, respiratory distress, rubella, respiratory tract, yellow and dengue Fever, aseptic meningitis, acute viral haemorrhagic illness, rabies, leukemia, HTLV-I-associated myelopathy, and AIDS.

Exemplary bacterial strains that infect human hosts include, but are not limited to: *Staphylococcus aureus, Streptococcus pneumoniae, Streptococcus pyogenes, Neisseria gonorrhoeae, Neisseria meningitides, Corynebacteria diphtherias, Bacillus anthracia, Listeria monocytogenes, Escherichia coli, Salmonella typhimurium, Salmonella typhae, Shigella, Campylobacter, Vibrio chloerae, Yersinia pestis, Pasteurella, Pseudomonas aeruginosa, Brucella Haemophilus, influenzae, Legionella, Bordetella, Clostridium tetani, Clostridium botulinum, Clostridium perfringens, Treponema pallidum, Borrelia burgdorferi, Leptospira interrogans, Mycobacterium tuberculosis, Mycobacterium leprae, Mycobacterium avium, Rickettsia prowazekii, Chlamydia trachomatis*, and *Mycoplasma pneumoniae*. The common names for some of the diseases or conditions caused by the bacteria listed above are: toxic shock syndrome, pneumonia, acute sinusitis, otitis media, meningitis, osteomyelitis, septic arthritis, endocarditis, peritonitis, pericarditis, cellulitis, brain abscess, tonsilitis, scarlet fever, glomerulonephritis, rheumatic fever, gonorrhoea, meningitis, diphtheria, anthrax, listeriosis, sepsis, gastroenteritis, typhoid fever, diarrhea, anorexia, salmonellosis, bacillary dysentery, Guillain-Barré syndrome, cholera, bubonic plague, cellulitis, wound infection, brucellosis, meningitis, bacteremia, cellulitis, osteomyelitis, epiglottitis, joint infection, sinusitis, Legionnaires' disease, pertussis or whooping cough, tetanus, botulism, tissue necrosis, bacteremia, emphysematous cholecystitis, gas gangrene, syphilis, kidney damage, Lyme arthritis, Lyme disease, tuberculosis, leprosy, typhus, rheumatoid arthritis, prostatitis, epididymitis, cervicitis, urethritis, and infertility.

Protozoa that infect human host include, but are not limited to: *Entamoeba histolytica, Giardia, Leishmania, Plasmodium (falciparum, vivax), Trypanosoma (brucei), Toxoplasma gondii,* and *Cryptosporidium.* Diseases/conditions caused by the protozoa listed above include, but are not limited to: Giardiasis, cutaneous (localized and diffuse) infections, visceral infections, fever, swelling of the liver and spleen, anemia, Malaria, sleeping sickness, Toxoplasmosis, and Cryptosporidiosis.

Fungi that infect human hosts include, but are not limited to: *Candida albicans, Cryptococcus neoformans, Aspergillus, Histoplasma capsulatum, Coccidioides immitis,* and *Pneumocystis carinii.* Diseases or conditions caused by the fungi listed above are: Candidiasis; skin, lung, and meningeal infections; fever, cough, chest pain or breathlessness; Histoplasmosis; Coccidioidomycosis (Valley Fever), and Pneumonia.

Worms that infect human hosts include, but are not limited to: *Trichuris trichiura, Trichinella spiralis, Enterobius vermicularis, Ascaris lumbricoides, Ancylostoma, Strongyloides, Filaria, Onchocerca volvulus, Loa loa, Dracuncula medinensis, Schistosoma (mansoni),* and *Clonorchis sinensis.* Diseases or conditions caused by worms listed above include, but are not limited to: human whipworm, roundworm, trichuriasis, Trichinosis, Pinworm, Ascariasis, Hookworm; intellectual, cognitive and growth retardation; intrauterine growth retardation, prematurity, and low birth weight; elephantiasis, Lymphatic Filariasis; river blindness; Calabar swellings; Dracunculiasis/Guinea worm disease (GWD); Schistosomiasis; liver and intestinal damage.

For example, the scaffold composition is packaged into a gelatin-coated pill and administered orally, releasing a multiple number of scaffold compositions within the gastrointestinal tract of the host subject. For diagnosis, collection of the scaffolds occur using a stool sample from the subject. This method of internalizing and collecting the device avoids exposure of the host and administrator to blood, which is particularly useful in regions of the world where blood-born viral infections, like AIDS, are prevalent. The device is alternatively introduced by intravenous, intraperitoneal, or intramuscular injections, as well as lumbar puncture, subcutaneous implantation, or surgical methods depending on the target site of interest.

Example 2: Capture and Collection of Circulating Mammalian Cells to Diagnose Disease The device is also used to diagnose disease caused by mammalian or eukaryotic cells, whereby it is administered into a host and collected. Following collection, the device is manipulated to yield its contents in order to allow for the identification of undesirable mammalian cells that circulate within the host, such as cancer cells undergoing metastasis from their primary tumor location, leukemia, lymphoma, sickle-shaped blood cells, or immune cells contributing to inflammation. Often a subject can be afflicted with primary cancer tumors affecting multiple organs all of which could metastasize and travel through the blood stream, lymphatic fluid, or cerebral spinal fluid (CSF). To quickly diagnose which tumor is contributing to the metastasis, and to avoid the unnecessary risk of surgery or multiple biopsies, the device is used to collect these cells for identification based either on molecular expression profiles or cell morphological features.

Example 3: Elimination of Neoplasms by Implantation of a Biodegradable Device

To counteract the growth of either malignant or benign neoplasms, which could become malignant, the device is implanted either by subcutaneous or intraperitoneal injection, or by surgical implantation, at the site of abnormally rapid cell replication. Once in place, the scaffold composition adheres to adjacent tissue and a bioactive composition that is either tethered to the scaffold or allowed to disseminate from the scaffold at close range, induces death of the rapidly dividing cell population. In this case, the scaffold degrades over time and does not require collection. A significant advantage of using the scaffold composition to reduce neoplastic growth, is that devices located around the tumor borders capture cells that attempt to escape from the tumor, thus, preventing them from spreading outside of their local niche.

Example 4: To Remove Blockages from Arterial Walls Using the Device as a Stent

To combat high blood pressure and minimize the risk of stroke, the device is introduced into the circulatory system by one of two methods: the scaffold is either used as an arterial stent in order to either remain stationary and allow the blood to pass through, or as a mobile device that flows along with blood in order to gain access to the entire body. As an arterial stent, the device reduces or eliminates the accumulation of compounds and/or cells that threaten to block the normal flow of blood. As a mobile device, the scaffold composition prevents the future occlusion of arteries by eliminating these compounds and/or cells before they can attach to the arterial walls.

Example 5: Device Implantation for the Permanent Removal of Adipocytes to Accomplish Life-Long Weight Loss Another use for the scaffold composition is "surgery-less liposuction." Many subjects are incapable of overcoming morbid obesity due to what is now considered a chemical addition to food. Methods to alter lifestyle and surgical intervention to limit the capacity of the body to intake calories have met with limited success. However, the elimination of adipocytes, or fat cells, from the body by means of destroying them locally, is more permanent solution the success of which does not depend upon the subject to maintain a proper diet. This therapeutic strategy relieves the chemical and physical threats that inflated adipocytes pose on the internal organs of morbidly obese subjects. To reduce or eliminate adipocytes, the scaffold composition is delivered by subcutaneous or intraperitoneal injection, or surgical

Example 6: Prevention of Glial Scars that Physically Prohibit Central Nerve Regeneration A unique property of the central nervous system, as opposed to the peripheral nervous system, is the inhibition of nerve regeneration. While researchers have identified the signaling molecules that prevent central nerve re-growth, Nogo ligands and their receptors, another factor that threatens the success of regenerative treatments is glial scarring. Glial cells, which normally support neuronal function, respond to nerve injury by increasing replication and invading the site of damage, thus forming a physical blockade against nerve outgrowth. The scaffold composition is delivered to the site of central nerve injury, and a bioactive composition is incorporated having means to specifically adhere, capture, and destroy glial cells that accumulate close to the site of nerve injury. Thus, the device prevents a glial scar from impeding regeneration. Furthermore, inhibitors of Nogo or blocking agents of the Nogo receptor diffuse from a bioactive composition further incorporated into the scaffold composition to eliminate molecular signals that would also inhibit regeneration.

Example 7: In Vivo Clearance of Amyloid Protein Plaques Associated with Alzheimer's Disease Current research into the field of neurodegenerative disease has provided important insights into the mechanisms behind some of our most debilitating diseases. For example, Alzheimer's Disease (AD) is tentatively diagnosed in living subjects based primarily on behavorial affects and, in some cases, genetic tests which can show predisposition only. The final diagnosis for AD is made postmortem, and the presence of protein plaques on the brain provides the final confirmation. To diagnose, retard, or arrest the formation of amyloid plaques in the brains of suspected AD patients, the device is injected into the cerebral spinal fluid by lumbar puncture wherein the scaffold composition contains immune cells capable of clearing cellular debris, and wherein the scaffold composition adheres to amyloid protein, thus allowing these resident cells to clear AD-related depositions. The devise is constructed of a non-biodegradable material and remains in the central nervous system to eliminate future deposits from accumulating.

Example 8: Prevention or Inhibition of Autoimmune Disease

Autoimmune disorders, e.g. those of the central nervous system are characterized by neurodegeneration and inappropriate immune system responses. For instance, multiple sclerosis is an autoimmune condition in which the host's immune system incorrectly recognizes nerve fibers as foreign cells, leading to their demyelination and, ultimately, to death of the host. To retard or arrest the progression of MS, the device is injected into the cerebral spinal fluid via lumbar puncture, or contacted to either brain or spinal cord tissue by surgical methods, wherein a bioactive composition incorporated into the scaffold composition, containing self-antigens (pre-isolated from the given subject) and chemokines, attracts, captures, and eliminates immune cells that contribute to immune system attacks of host tissues.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of removing or eliminating an autoimmune cell from a mammalian subject, comprising
   a) administering to the subject a device comprising a hydrogel composition and a bioactive composition, wherein the bioactive composition is incorporated into or conjugated onto the hydrogel composition, wherein the hydrogel composition comprises a polymer matrix and pores, and wherein the bioactive composition comprises a self-antigen pre-isolated from the subject;
   b) exposing the autoimmune cell to the self-antigen, thereby recruiting the autoimmune cell to the hydrogel composition, wherein the autoimmune cell is predisposed to recognize the self-antigen as foreign;
   c) capturing the autoimmune cell within the hydrogel composition, thereby sequestering the autoimmune cell from the host environment; and
   d) removing or eliminating the captured autoimmune cell from the subject.

2. The method of claim 1, wherein the device is administered orally, systemically, intravenously, intraperitoneally, by intramuscular injection, by lumbar puncture to access cerebral spinal fluid, subcutaneously, transcutaneously, or surgically.

3. The method of claim 1, further comprising the step of collecting the device from the subject.

4. The method of claim 1, wherein the device is not collected from the subject.

5. The method of claim 1, wherein the self-antigen is isolated from a tissue of the subject.

6. The method of claim 1, wherein the self-antigen is a surface antigen.

7. The method of claim 1, wherein the subject has an autoimmune disease.

8. The method of claim 7, wherein the autoimmune disease is multiple sclerosis.

9. The method of claim 7, wherein the autoimmune disease is diabetes.

10. The method of claim 1, further comprising killing the sequestered autoimmune cell within the hydrogel composition.

11. The method of claim 10, wherein the sequestered autoimmune cell is killed by exposure to the hydrogel composition.

12. The method of claim 1, wherein the device further comprises a cell-death inducing agent.

13. The method of claim 12, further comprising killing the sequestered autoimmune cell by exposure to the cell-death inducing agent.

14. The method of claim 12, wherein the cell-death inducing agent comprises an engineered virus, a humanized monoclonal antibody to activate the immune system, a pro-apoptotic ligand, a radioactive isotope, a toxin, or a chemotherapeutic agent.

15. The method of claim 14, wherein the pro-apoptotic ligand comprises FasL, TNF, TRAIL, or a caspase activator.

16. The method of claim 14, wherein the radioactive isotope comprises Bismuth-213, Holmium-66, Iodine-125, Iodine-131, or Lutetium-177.

17. The method of claim 14, wherein the toxin comprises a hemotoxin, a necrotoxin, or a neurotoxin.

18. The method of claim 1, wherein the polymer comprises poly(lactide-co-glycolide)(PLGA).

19. The method of claim 1, wherein the size of the pores is less than about 10 nm, in the range of 100 nm to 2 µM, or greater than about 20 µM in diameter.

20. The method of claim 17, wherein the size of the pores is about 400 µM to 500 µM in diameter.

21. The method of claim 1, wherein the bioactive composition further comprises an additional cell-attractant.

22. The method of claim 21, wherein the cell attractant is selected from the group consisting of a multivalent acrylamide polymer linked to a sugar, a polylysine linked to a sugar, a cytokine, a chemokine, or a combination thereof.

23. The method of claim 22, wherein the cell attractant comprises a cytokine, a chemokine, or a combination thereof.

24. The method of claim 1, wherein the bioactive composition further comprises a signaling protein to either induce cell death or prevent further immune responses.

25. The method of claim 1, wherein the captured autoimmune cell is removed or eliminated by degradation of the captured autoimmune cell within the hydrogel composition.

26. The method of claim 1, wherein the captured autoimmune cell is removed or eliminated by collection of the hydrogel composition from the subject.

* * * * *

SEQUENCE LISTING

```
<160> NUMBER OF SEQ ID NOS: 17

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Gly Gly Gly Gly Arg Gly Asp Ser Pro
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(3)
<223> OTHER INFORMATION: Xaa is any basic amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa is any basic amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 2

Xaa Xaa Xaa Xaa Xaa Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Pro Arg Arg Ala Arg Val
1               5

<210> SEQ ID NO 4
<211> LENGTH: 19
<212> TYPE: PRT
<213> ORGANISM: Artificial Sequence
<220> FEATURE:
<223> OTHER INFORMATION: Synthetic

<400> SEQUENCE: 4

Tyr Glu Lys Pro Gly Ser Pro Pro Arg Glu Val Val Pro Arg Pro Arg
1               5                   10                  15

Pro Gly Val

<210> SEQ ID NO 5
<211> LENGTH: 28
<212> TYPE: PRT
<213> ORGANISM: Artificial Sequence
<220> FEATURE:
<223> OTHER INFORMATION: Synthetic

<400> SEQUENCE: 5

Arg Pro Ser Leu Ala Lys Lys Gln Arg Phe Arg His Arg Asn Arg Lys
1               5                   10                  15

Gly Tyr Arg Ser Gln Arg Gly His Ser Arg Gly Arg
            20                  25

<210> SEQ ID NO 6
<211> LENGTH: 17
<212> TYPE: PRT
<213> ORGANISM: Artificial Sequence
<220> FEATURE:
<223> OTHER INFORMATION: Synthetic

<400> SEQUENCE: 6
```

```
Arg Ile Gln Asn Leu Leu Lys Ile Thr Asn Leu Arg Ile Lys Phe Val
1               5                   10                  15

Lys

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Leu Arg Gly Asp Asn
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Ile Lys Val Ala Val
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Tyr Ile Gly Ser Arg
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Pro Asp Ser Gly Arg
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic

<400> SEQUENCE: 11

Arg Asn Ile Ala Glu Ile Ile Lys Asp Ala
1               5                   10

<210> SEQ ID NO 12
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 12

Arg Gly Asp Ser
1

<210> SEQ ID NO 13
<211> LENGTH: 4
<212> TYPE: PRT
<213> ORGANISM: Artificial Sequence
<220> FEATURE:
<223> OTHER INFORMATION: Synthetic

<400> SEQUENCE: 13

Arg Glu Asp Val
1

<210> SEQ ID NO 14
<211> LENGTH: 4
<212> TYPE: PRT
<213> ORGANISM: Artificial Sequence
<220> FEATURE:
<223> OTHER INFORMATION: Synthetic

<400> SEQUENCE: 14

Arg Gly Asp Val
1

<210> SEQ ID NO 15
<211> LENGTH: 4
<212> TYPE: PRT
<213> ORGANISM: Artificial Sequence
<220> FEATURE:
<223> OTHER INFORMATION: Synthetic

<400> SEQUENCE: 15

Arg Gly Asp Thr
1

<210> SEQ ID NO 16
<211> LENGTH: 4
<212> TYPE: PRT
<213> ORGANISM: Artificial Sequence
<220> FEATURE:
<223> OTHER INFORMATION: Synthetic

<400> SEQUENCE: 16

Asp Gly Glu Ala
1

<210> SEQ ID NO 17
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 17

Val Thr Xaa Gly
1
```